US008927674B2

(12) United States Patent
Atienza et al.

(10) Patent No.: US 8,927,674 B2
(45) Date of Patent: Jan. 6, 2015

(54) DEHYDROGENATIVE SILYLATION AND CROSSLINKING USING COBALT CATALYSTS

(71) Applicants: Momentive Performance Materials Inc., Waterford, NY (US); Princeton University, Princeton, NJ (US)

(72) Inventors: Cristia Carmen Hojilla Atienza, Princeton, NJ (US); Paul J. Chirik, Princeton, NJ (US); Susan Nye, Feura Bush, NY (US); Kenrick M. Lewis, Flushing, NY (US); Keith J. Weller, Rensselaer, NY (US); Julie L. Boyer, Watervliet, NY (US); Johannes G. P. Delis, Bergen op Zoom (NL); Aroop Roy, Mechanicville, NY (US); Eric Pohl, Mount Kisco, NY (US)

(73) Assignees: Princeton University, Princeton, NJ (US); Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 13/966,568

(22) Filed: Aug. 14, 2013

(65) Prior Publication Data

US 2014/0051822 A1 Feb. 20, 2014

Related U.S. Application Data

(60) Provisional application No. 61/819,753, filed on May 6, 2013, provisional application No. 61/683,882, filed on Aug. 16, 2012.

(51) Int. Cl.
| | | |
|---|---|---|
| *C08G 77/12* | (2006.01) | |
| *C07F 7/08* | (2006.01) | |
| *B01J 31/18* | (2006.01) | |
| *C07F 7/18* | (2006.01) | |
| *C08G 77/38* | (2006.01) | |
| *C07F 15/06* | (2006.01) | |
| *C08G 77/20* | (2006.01) | |

(52) U.S. Cl.
CPC ............. *C07F 15/065* (2013.01); *C07F 7/0829* (2013.01); *B01J 2531/845* (2013.01); *C07F 7/0879* (2013.01); *B01J 2231/323* (2013.01); *B01J 31/1815* (2013.01); *C07F 7/1876* (2013.01); *C08G 77/38* (2013.01); *B01J 2531/0241* (2013.01)
USPC ............. 528/31; 502/152; 502/159; 502/161; 528/14; 585/631; 585/654

(58) Field of Classification Search
USPC ....................... 528/14, 31; 502/152, 159, 161; 585/631, 654
See application file for complete search history.

(56) References Cited

U.S. PATENT DOCUMENTS

| | | |
|---|---|---|
| 3,159,601 A | 12/1964 | Ashby |
| 3,220,972 A | 11/1965 | Lamoreaux |
| 3,775,452 A | 11/1973 | Karstedt |
| 5,955,555 A | 9/1999 | Bennett |
| 6,461,994 B1 | 10/2002 | Gibson et al. |
| 6,657,026 B1 | 12/2003 | Kimberley et al. |
| 7,053,020 B2 | 5/2006 | De Boer et al. |
| 7,148,304 B2 | 12/2006 | Kimberley et al. |
| 7,442,819 B2 | 10/2008 | Ionkin et al. |
| 2011/0009573 A1 | 1/2011 | Delis et al. |

FOREIGN PATENT DOCUMENTS

WO    WO 2012071359    5/2012

OTHER PUBLICATIONS

Bogdan Marciniec et al., "Competitive silylation of olefins with vinylsilanes and hydrosilanes photocatalyzed by iron carbonyl complexes", Inorg. Chem. Commun. 2000, 3, 371-375, Poznan, Poland.
Roman N. Naumov et al., "Selective Dehydrogentative Silylation-Hydrogenation Reaction of Divinyldisiloxane with Hydrosilane Catalyzed by an Iron Complex", Journal of the American Chemical Society, 2012, vol. 134, Issue 2, 804-807, Osaka, Japan.
Michael P, Doyle et al., "Addition/Elimination in the Rhodium(II) Perfluorobutyrate Catalyzed Hydrosilylationo f 1-Alkenes. Rhodium Hydride Promoted Isomerization and Hydrogenation", Organometallics, 1992, 11, 549-555, San Antonio, Texas.
Biao Lu et al., "Iridium-Catalyzed (Z)-Trialkylsilylation of Terminal Olefins", J. Org. Chem, 2010, 75, 1701-1705, Dallas, Texax.
Yoji Hori et al., "Ruthenium Complex-Catalyzed Silylation of Olefins. Selective Sysnthesis of Allysilanes", Bull. Chem. Soc. Jpn., 1988, 61, 3011-3013, Kyoto, Japan.
L.A. Oro et al., "Hydrosilylation of Alkenes by Iridium Complexes", J. Mol. Catalysis, 1986, 37, 151-156, Saragossa, Spain.
Maria J. Fernandez et al., "Synthesis and Reactions of Dihydrido(triethylsily1)(1,5-cyclooctadiene)-Iridium(III) Complexes: Catalysts for Dehydrogenative Silylation of Alkenes", Am. Chem. Soc., Organometallics 1986, 5, 1519-1520, Zaragoza, Spain.
Yoshio Seki et al., "Single-Operation Synthesis of Vinylsilanes from Alkenes and Hydrosilanes with the Aid of Ru3 (CO)12", Am. Chem. Soc., J. Org. Chem. 1986, 51, 3890-3895, Osaka, Japan.
Fumitoshi Kakiuchi et al., "Dehydrogenative Silylation of 1,5-Dienes with Hydrosilanes Catalyzed by RhCl (PPh3)3", Am. Chem. Soc., Organometallics, 1993, 12, 4748-4750, Kagawa, Japan.
Hideo Nagashima et al., "Dehydrogenative Silylation of Ketones with a Bifunctional Organosilane by Rhodium-Pybox Catalysts", Chem. Soc. of Jpn., Chemistry Letters, 1993, 347-350, Toyohashi, Aichi.
Rick Jairam et al., "Ester Hydrolysis with 2,6-di(pyrazol-3-yl)pyridines and their Co 11 Complexes in Homogeneous and Micellar Media", Journal of Inorganic Biochemistry 84, 2001, 113-118, Toronto, Ontario, Canada.

(Continued)

*Primary Examiner* — Terressa Boykin
(74) *Attorney, Agent, or Firm* — Joseph S. Ostroff, Esq.; McDonald Hopkins LLC

(57) ABSTRACT

Disclosed herein are cobalt complexes containing terdentate pyridine di-imine ligands and their use as efficient and selective dehydrogenative silylation and crosslinking catalysts.

65 Claims, No Drawings

(56) References Cited

OTHER PUBLICATIONS

Ines Glatz, et al., "Terpyridine-Based Silica Supports Prepared by Ring-Opening Metathesis Polymerization for the Selective Extraction of Noble Metals", Journal of Chromatography A 2003, 1015, 65-71, Austria.

Speier, J.Y. et al., "The Addition of Silicon Hydrides to Olefinic Double Bonds. Part II. The Use of Group VIII Metal Catalysts", Am. Chem. Soc. 1957, 79, 974-979, Easton, Pennsylvania.

Roswitha Kroll, "Access to Heterogeneous Atom-Transfer Radica Polymerization (ATRP) Catalysts Based on Dipyridylamine and Terpyridine via Ring-Opening Metathesis Polymerization (ROMP)", Macromol. Chem. Phys. 2001, 202, No. 5, 645-653.

Chungkyun Kim et al., "2,2':6',2''-Terpyridine and bis(2,2,':6',2''-terpyridine)ruthenium(II) Complex on the Dendritic Periphery", Journal of Organometallic Chemistry 2003, 673, 77-83.

Nesmeyanov, A.N. et al., "Addition, Substitution, and Telomerization Reactions of Olefins in the Presence of Metal Carbonyls or Colloidal Iron", Tetrahedron 1962, 17, 61-68.

Fumitoshi Kakiuchi et al., "Completely Selective Synthesis of (E)-B-(triethylsilyl)styrenes by Fe3(CO)12-catalyzed Reaction of Styrenes With Triethylsilane", Journal of Organometallic Chemistry 1993, 456, 45-47, Osaka, Japan.

Jesse R. McAtee et al., "Preparation of Allyl and Vinyl Silanes by the Palladium-Catalyzed Silylation of Terminal Olefins: A Silyl-Heck Reaction**", Angewandte Chemie, Int. Ed. 2012, 51, 3663-3667.

Amanda C. Bowman et al., "Reduced N-Alkyl Substituted Bis(imino)pyridine Cobalt Complexes: Molecular and Electronic Structures for Compounds Varying by Three Oxidation States", Inorg. Chem. 2010, 49, 6110-6123, Germany.

Neil G. Connelly et al., "Chemical Redox Agents for Organometallic Chemistry", Chem. Rev. 1996, 96, 877-910, Burlington, Vermont.

Amy B. Pangborn et al., "Safe and Convenient Procedure for Solvent Purification", Organometallics 1996, 15, 1518-1520, Midland, Michigan.

Amanda C. Bowman et al., "Synthesis and Molecular and Electronic Structures of Reduced Bis(imino) pyridine Cobalt Dinitrogen Complexes: Ligand versus Metal Reduction", J. Am. Chem. Soc., 2010, 132, 1676-1684, Germany.

Martin J. Humphries et al., "Investigations into the Mechanism of Activation and Initiation of Ethylene Polymerization by Bis(imino)pyridine Cobalt Catalysts: Synthesis, Structures, and Deuterium Labeling Studies", OrganmetallIcs 2005, 24, 2039-2050, London, United Kingdom.

European Extended Search Report, EP 13 180 637.4, Oct. 17, 2013.

Crisita Carmen H. Atienza, Paul J. Chirik, "2-Olefin hydrosilylation and dehydrogenative silylation with bis(imino) pyridine iron and cobalt catalysts", www.cen-online.org, Jun. 25, 2012, p. 51.

Vernon C. Gibson, Martin J. Humphries, Kilian P. Tellmann, Duncan F. Wass, Andrew J.P. Whjite and David J. Williams, "The nature of the active species in bis(imino)pyridyl cobalt ethylene polymerisation catalysts," Chem. Commun., 2001, 2252-2253.

Mohammad G. Dekamin, Kambiz Varmira, Mehdi Farahmand, Solmaz Sagheb-Asl, Zahra Karimi, "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis Communications 12 (2010) 226-230.

Crisita Carmen Hojilla Atienza, Carsten Milsmann, Emil Lobkovsky, and Paul J. Chirik, "Sythesis, Electronic Structure, and Ethylene Polymerization Activity of Bis(imino)pyridine Cobalt Alkyl Cations," Agnewandte Chem. Int. Ed. 2011, 50, 8143-8147.

DEHYDROGENATIVE SILYLATION AND CROSSLINKING USING COBALT CATALYSTS

CROSS-REFERENCE TO RELATED APPLICATIONS

This application claims the benefit of U.S. Provisional Application 61/683,882 filed Aug. 16, 2012 and U.S. Provisional Application 61/819,753 filed May 6, 2013. These applications are incorporated by reference herein in their entireties.

FIELD OF THE INVENTION

This invention relates generally to transition metal-containing compounds, more specifically to cobalt complexes containing pyridine di-imine ligands and their use as efficient dehydrogenative silylation and crosslinking catalysts.

BACKGROUND OF THE INVENTION

Hydrosilylation chemistry, typically involving a reaction between a silyl hydride and an unsaturated organic group, is the basis for synthetic routes to produce commercial silicone-based products like silicone surfactants, silicone fluids and silanes as well as many addition cured products like sealants, adhesives, and silicone-based coating products. See, for example, US Patent Application Publication 2011/0009573A1 to Delis et al. Typical hydrosilylation reactions use precious metal catalysts to catalyze the addition of a silyl-hydride (Si—H) to an unsaturated group, such as an olefin. In these reactions, the resulting product is a silyl-substituted, saturated compound. In most of these cases, the addition of the silyl group proceeds in an anti-Markovnikov manner, i.e., to the less substituted carbon atom of the unsaturated group. Most precious metal catalyzed hydrosilylations only work well with terminally unsaturated olefins, as internal unsaturations are generally non-reactive or only poorly reactive. There are currently only limited methods for the general hydrosilylation of olefins where after the addition of the Si—H group there still remains an unsaturation in the original substrate. This reaction, termed a dehydrogenative silylation, has potential uses in the synthesis of new silicone materials, such as silanes, silicone fluids, crosslinked silicone elastomers, and silylated or silicone-crosslinked organic polymers such as polyolefins, unsaturated polyesters, and the like.

Various precious metal complex catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

There are examples of the use of $Fe(CO)_5$ to promote limited hydrosilylations and dehydrogenative silylations. (See Nesmeyanov, A. N.; Freidlina, R. Kh.; Chukovskaya, E. C.; Petrova, R. G.; Belyaysky, A. B. *Tetrahedron* 1962, 17, 61 and Marciniec, B.; Majchrzak, M. *Inorg. Chem. Commun.* 2000, 3, 371). The use of $Fe_3(CO)_{12}$ was also found to exhibit dehydrogenative silylation in the reaction of $Et_3SiH$ and styrene. (Kakiuchi, F.; Tanaka, Y.; Chatani, N.; Murai, S. *J. Organomet. Chem.* 1993, 456, 45). Also, several cyclopentadiene iron complexes have been used to varying degrees of success, with the work of Nakazawa, et at showing interesting intramolecular dehydrogenative silylation/hydrogenation when used with 1,3-di-vinyldisiloxanes. (Roman N Naumov, Masumi Itazaki, Masahiro Kamitani, and Hiroshi Nakazawa, *Journal of the American Chemical Society,* 2012, Volume 134, Issue 2, Pages 804-807).

A rhodium complex was found to give low to moderate yields of allyl-silanes and vinyl silanes. (Doyle, M. P.; Devora G. A.; Nevadov, A. O.; High, K. G. *Organometallics,* 1992, 11, 540-555). An iridium complex was also found to give vinyl silanes in good yields. (Falck, J. R.; Lu, B, *J. Org Chem,* 2010, 75, 1701-1705.) Allyl silanes could be prepared in high yields using a rhodium complex (Mitsudo, T.; Watanabe, Y.; Hori, Y. Bull. Chem. Soc. Jpn. 1988, 61, 3011-3013). Vinyl silanes could be prepared through the use of a rhodium catalyst (Murai, S.; Kakiuchi, F.; Nogami, K.; Chatani, N.; Seki, Y. *Organometallics,* 1993, 12, 4748-4750). Dehydrogenative silylation was found to occur when iridium complexes were used (Oro, L. A.; Fernandez, M. J.; Esteruelas, M. A.; Jiminez, M. S. *J. Mol. Catalysis,* 1986, 37, 151-156 and Oro, L. A.; Fernandez, M. J.; Esteruelas, M. A.; Jiminez, M. S. *Organometallics,* 1986, 5, 1519-1520). Vinyl silanes could also be produced using ruthenium complexes (Murai, S.; Seki, Y.; Takeshita, K.; Kawamoto, K.; Sonoda, N. *J. Org. Chem.* 1986, 51, 3890-3895.).

A palladium-catalyzed silyl-Heck reaction was recently reported to result in the formation of allyl-silanes and vinyl silanes (McAtee J R, et al., *Angewandte Chemie, International Edition in English* (2013, 51, 3663-3667 (Apr. 10, 2012)).

U.S. Pat. No. 5,955,555 discloses the synthesis of certain iron or cobalt pyridine di-imine (PDI) dianion complexes. The preferred anions are chloride, bromide and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. Chirik et al describe bisarylimino pyridine cobalt anion complexes (Inorg. Chem. 2010, 49, 6110 and JACS. 2010, 132, 1676.) However, the catalysts and catalyst systems disclosed in these references are described for use in the context of olefin hydrogenation, polymerizations and/or oligomerisations, not in the context of dehydrogenative silylation reactions.

There is a continuing need in the silylation industry for non-precious metal-based catalysts that are effective for efficiently and selectively catalyzing dehydrogenative silylations. The present invention provides one answer to that need.

Further, many industrially important homogeneous metal catalysts suffer from the drawback that following consumption of the first charge of substrates, the catalytically active metal is lost to aggregation and agglomeration whereby its beneficial catalytic properties are substantially diminished via colloid formation or precipitation. This is a costly loss, especially for noble metals such as Pt. Heterogeneous catalysts are used to alleviate this problem but have limited use for polymers and also have lower activity than homogeneous counterparts. For example, it is well-known in the art and in the hydrosilylation industry that the two primary homogeneous catalysts, Speier's and Karstedt's, often lose activity after catalyzing a charge of olefin and silyl- or siloxyhydride reaction. If a single charge of the homogeneous catalyst could be re-used for multiple charges of substrates, then catalyst and process cost advantages would be significant.

SUMMARY OF THE INVENTION

In one aspect, the present invention is directed to a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof;

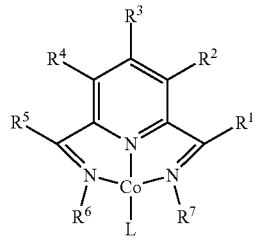

(I)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and L is hydroxyl, chloride, bromide, or a C1-C18 alkyl, C1-C18 substituted alkyl, aryl, or substituted aryl group, an alkaryl group, an aralkyl group, —H, $SiR_3$ where R is an alkyl, aryl, or siloxanyl group, or component (a) wherein L optionally contains at least one heteroatom.

In another aspect, the present invention is directed to a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex selected from the group consisting of Formula (IV), Formula (V), Formula (VI), Formula (VII), or an adduct thereof.

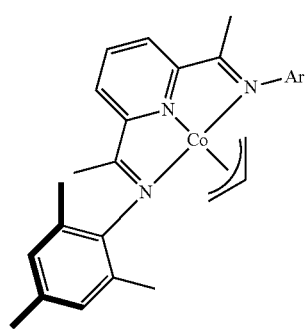

(Formula IV)

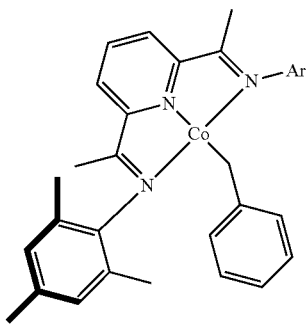

(Formula V)

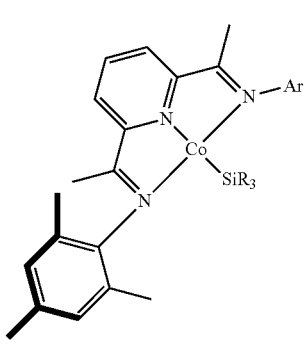

(Formula VI)

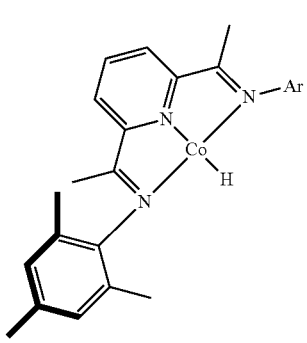

(Formula VII)

wherein R is an alkyl, aryl, or siloxanyl group.

In another aspect, the present invention is directed to a compound of Formula (II)

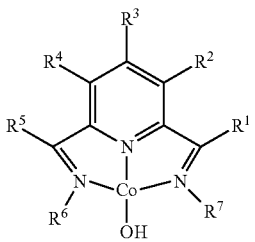

(II)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; and optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure.

In another aspect, the present invention is directed to a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (III) or an adduct or salt thereof;

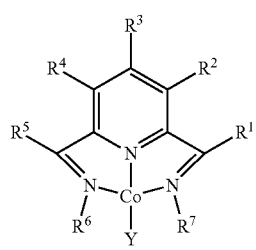

(III)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; Y is a neutral ligand optionally containing at least one heteroatom; and wherein Formula III is a neutral, cationic, or anionic complex.

In another aspect, the present invention is directed to a process for producing a crosslinked material, comprising reacting a mixture comprising (a) a silyl-hydride containing polymer, (b) a mono-unsaturated olefin or an unsaturated polyolefin, or combinations thereof and (c) a catalyst, optionally in the presence of a solvent, in order to produce the crosslinked material, wherein the catalyst is a complex of the Formula (I) or an adduct thereof;

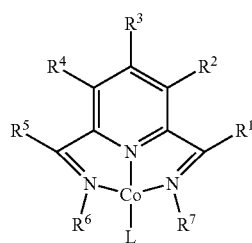

(I)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and L is hydroxyl, chloride, bromide, or a C1-C18 alkyl, C1-C18 substituted alkyl, aryl, or substituted aryl group, an alkaryl group, an aralkyl group, —H, $SiR_3$ where R is an alkyl, aryl, or siloxanyl group, or component (a) wherein L optionally contains at least one heteroatom.

DETAILED DESCRIPTION OF THE INVENTION

The invention relates to cobalt complexes containing pyridine di-imine ligands and their use as efficient dehydrogenative silylation and crosslinking catalysts. In one embodiment of the invention, there is provided a complex of the Formulae (I), (II), or (III) as illustrated above, wherein Co in any valence or oxidation state (e.g., +1, +2, or +3) for use in said dehydrogenative silylation and crosslinking reactions. In particular, according to one embodiment of the invention, a class of cobalt pyridine di-imine complexes has been found that are capable of dehydrogenative silylation reactions. The invention also addresses the advantage of reusing a single charge of catalyst for multiple batches of product, resulting in process efficiencies and lower costs.

By "alkyl" herein is meant to include straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially or deleteriously interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

By "alkenyl" herein is meant any straight, branched, or cyclic alkenyl group containing one or more carbon-carbon double bonds, where the point of substitution can be either a carbon-carbon double bond or elsewhere in the group. Specific and non-limiting examples of alkenyls include, but are not limited to, vinyl, propenyl, allyl, methallyl, ethylidenyl norbornane.

By "alkynyl" is meant any straight, branched, or cyclic alkynyl group containing one or more carbon-carbon triple bonds, where the point of substitution can be either at a carbon-carbon triple bond or elsewhere in the group.

By "unsaturated" is meant one or more double or triple bonds. In a preferred embodiment, it refers to carbon-carbon double or triple bonds.

By "inert substituent" herein is meant a group other than hydrocarbyl or substituted hydrocarbyl, which is inert under the process conditions to which the compound containing the group is subjected. The inert substituents also do not substantially or deleteriously interfere with any process described herein that the compound in which they are present may take part in. Examples of inert substituents include halo (fluoro, chloro, bromo, and iodo), ether such as —$OR^{30}$ wherein $R^{30}$ is hydrocarbyl or substituted hydrocarbyl.

By "hetero atoms" herein is meant any of the Group 13-17 elements except carbon, and can include for example oxygen, nitrogen, silicon, sulfur, phosphorus, fluorine, chlorine, bromine, and iodine.

By "olefin" herein is meant any aliphatic or aromatic hydrocarbon also containing one or more aliphatic carbon-carbon unsaturations. Such olefins may be linear, branched or cyclic and may be substituted with heteroatoms as described above, with the proviso that the substitutents do not interfere substantially or deleteriously with the course of the desired reaction to produce the dehydrogenatively silylated product.

In one embodiment, the unsaturated compound useful as a reactant in the dehydrogenative silylation is an organic compound having the structural group, $R_2C$=$C$—$CHR$, where R is an organic fragment or hydrogen.

As indicated above, the present invention is directed to a process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof;

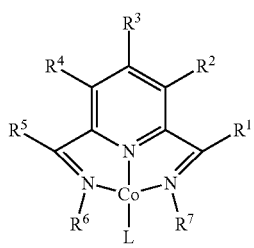

(I)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom; each occurrence of $R^6$ and $R^7$ is independently C1-C18 alkyl, C1-C18 substituted alkyl, aryl or substituted aryl, wherein $R^6$ and $R^7$ optionally contain at least one heteroatom; optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and L is hydroxyl, chloride, bromide, or a C1-C18 alkyl, C1-C18 substituted alkyl, aryl, or substituted aryl group, an alkaryl group, an aralkyl group, —H, $SiR_3$ where R is an alkyl, aryl, or siloxanyl group, or component (a) wherein L optionally contains at least one heteroatom.

The catalyst utilized in the process of the present invention is illustrated in Formula (I) above wherein Co is in any valence or oxidation state (e.g., +1, +2, or +3). In one embodiment, at least one of $R^6$ and $R^7$ is

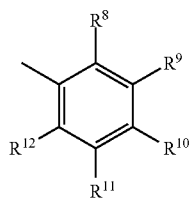

wherein each occurrence of $R^8$, $R^9$, $R^{10}$, $R^{11}$, and $R^{12}$ is independently hydrogen, C1-C18 alkyl, C1-C18 substituted alkyl, aryl, substituted aryl, or an inert substituent, wherein $R^8$-$R^{12}$, other than hydrogen, optionally contain at least one heteroatom. $R^8$ and $R^{12}$ may further include independently methyl, ethyl or isopropyl groups and $R^{10}$ may be hydrogen or methyl. In one particularly preferred embodiment, $R^8$, $R^{10}$, and $R^{12}$ are each methyl; $R^1$ and $R^5$ may independently be methyl or phenyl groups; and $R^2$, $R^3$ and $R^4$ may be hydrogen.

One particularly preferred embodiment of the catalyst of the process of the invention is the compound of Formula (II)

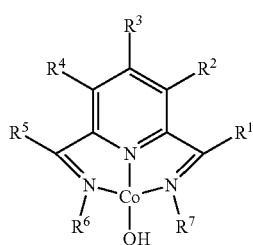

(II)

wherein
each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;
each occurrence of $R^6$ and $R^7$ is independently C1-C18 alkyl, C1-C18 substituted alkyl, aryl or substituted aryl, wherein $R^6$ and $R^7$ optionally contain at least one heteroatom; and
optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure.

In an alternative embodiment, the catalyst utilized in the process of the present invention may be in the form of Formula (III) or an adduct or salt thereof;

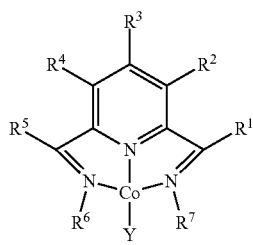

(III)

wherein
$R^1$-$R^7$ are as described for Formula I and
Y is a neutral ligand optionally containing at least one heteroatom;

wherein Formula III is a neutral, cationic, or anionic complex.

As defined herein, the phrase "neutral ligand" means any ligand without a charge. Examples of neutral ligands Y include dinitrogen ($N_2$), phosphines, CO, nitrosyls, olefins, amines, and ethers. Specific examples of Y include, but are not limited to $PH_3$, $PMe_3$, CO, NO, ethylene, THF, and $NH_3$.

Other preferred embodiments of the catalysts of the process of the invention include the catalysts having the structures of Formula (IV), Formula (V), Formula (VI), Formula (VII), or an adduct thereof:

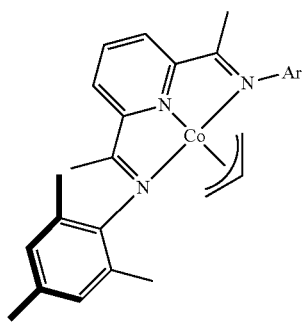
(Formula IV)

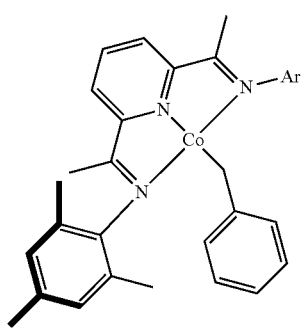
(Formula V)

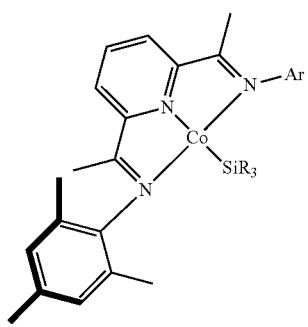
(Formula VI)

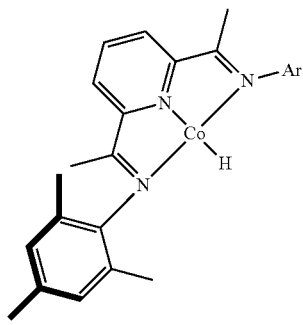
(Formula VII)

wherein R is an alkyl, aryl, or siloxanyl group.

Various methods can be used to prepare the catalyst utilized in the process of the present invention. In one embodiment, the catalyst is generated in-situ by contacting a catalyst precursor with an activator in the presence of a liquid medium containing at least one component selected from the group consisting of a solvent, the silyl hydride, the compound containing at least one unsaturated group, and combinations thereof, wherein the catalyst precursor is represented by structural Formula (VIII)

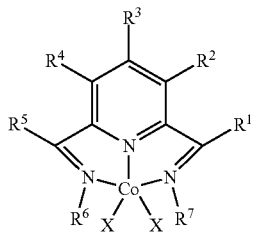
(VIII)

wherein
each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;
each occurrence of $R^6$ and $R^7$ is independently C1-C18 alkyl, C1-C18 substituted alkyl, aryl or substituted aryl, wherein $R^6$ and $R^7$ optionally contain at least one heteroatom;
optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and
X is an anion selected from the group consisting of $F^-$, $Cl^-$, $Br^-$, $I^-$, $CF_3R^{40}SO_3^-$ or $R^{50}COO^-$, wherein $R^{40}$ is a covalent bond or a C1-C6 alkylene group, and $R^{50}$ is a C1-C10 hydrocarbyl group.

The activator may be a reducing agent or an alkylating agent such as $NaHBEt_3$, $CH_3Li$, DIBAL-H, LiHMDS, MeMgBr, EtMgCl, as well as combinations thereof. Preferably, the reducing agent has a reduction potential more negative than -0.6 v (versus ferrocene, as described in Chem. Rev. 1996, 96, 877-910. A larger negative number represents a larger reduction potential). Preferably, the reduction potential ranges from -0.76 V to -2.71V. The most preferred reducing agents have a reduction potential in the range of -2.8 to -3.1 V.

The methods to prepare the catalysts are known to a person skilled in the field. For example, the catalysts can be prepared by reacting a PDI ligand with a metal halide, such as $FeBr_2$ as disclosed in US Patent Application Publication 2011/0009573A1. Typically, the PDI ligands are produced through condensation of an appropriate amine or aniline with 2,6-diacetylpyridine and its derivatives. If desired, the PDI ligands can be further modified by known aromatic substitution chemistry.

In the process of the invention, the catalysts can be unsupported or immobilized on a support material, for example, carbon, silica, alumina, $MgCl_2$ or zirconia, or on a polymer or prepolymer, for example polyethylene, polypropylene, polystyrene, poly(aminostyrene), or sulfonated polystyrene. The metal complexes can also be supported on dendrimers.

In some embodiments, for the purposes of attaching the metal complexes of the invention to a support, it is desirable that at least one of $R^1$ to $R^9$ of the metal complexes, preferably $R^6$, has a functional group that is effective to covalently bond to the support. Exemplary functional groups include but are not limited to SH, COOH, NH$_2$ or OH groups.

In one embodiment, silica supported catalyst may be prepared via Ring-Opening Metathesis Polymerization (ROMP) technology as discussed in the literature, for example Macromol. Chem. Phys. 2001, 202, No. 5, pages 645-653; Journal of Chromatography A, 1025 (2003) 65-71.

One way to immobilize catalysts on the surface of dendrimers is by the reaction of Si—C bonded parent dendrimers and functionalized PDI in the presence of a base is as illustrated by Kim et al. in Journal of Organometallic Chemistry 673 (2003) 77-83.

The unsaturated compound containing at least one unsaturated functional group utilized in the process of the invention can be a compound having one, two, three, or more unsaturations. Examples of such unsaturated compounds include an olefin, a cycloalkene, unsaturated polyethers such as an alkyl-capped allyl polyether, a vinyl-functional alkyl-capped allyl or methallyl polyether, an alkyl-capped terminally unsaturated amine, an alkyne, terminally unsaturated acrylate or methacrylate, unsaturated aryl ether, vinyl-functionalized polymer or oligomer, vinyl-functionalized silane, vinyl-functionalized silicone, unsaturated fatty acids, unsaturated esters, and combinations thereof.

Unsaturated polyethers suitable for the dehydrogenative silylation reaction preferably are polyoxyalkylenes having the general formula:

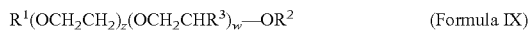

R$^1$(OCH$_2$CH$_2$)$_z$(OCH$_2$CHR$^3$)$_w$—OR$^2$ (Formula IX)

or

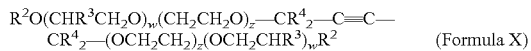

R$^2$O(CHR$^3$CH$_2$O)$_w$(CH$_2$CH$_2$O)$_z$—CR$^4{}_2$—C≡C—
    CR$^4{}_2$—(OCH$_2$CH$_2$)$_z$(OCH$_2$CHR$^3$)$_w$R$^2$ (Formula X)

or

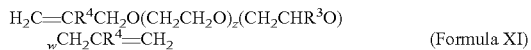

H$_2$C=CR$^4$CH$_2$O(CH$_2$CH$_2$O)$_z$(CH$_2$CHR$^3$O)$_w$CH$_2$CR$^4$=CH$_2$ (Formula XI)

wherein R$^1$ denotes an unsaturated organic group containing from 2 to 10 carbon atoms such as allyl, methylallyl, propargyl or 3-pentynyl. When the unsaturation is olefinic, it is desirably terminal to facilitate smooth dehydrogenative silylation. However, when the unsaturation is a triple bond, it may be internal. R$^2$ is hydrogen, vinyl, or a polyether capping group of from 1 to 8 carbon atoms such as the alkyl groups: CH$_3$, n-C$_4$H$_9$, t-C$_4$H$_9$ or i-C$_8$H$_{17}$, the acyl groups such as CH$_3$COO, t-C$_4$H$_9$COO, the beta-ketoester group such as CH$_3$C(O)CH$_2$C(O)O, or a trialkylsilyl group. R$^3$ and R$^4$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl or aralkyl groups, for example, benzyl, phenylethyl and nonylphenyl, or the cycloalkyl groups, for example, cyclohexyl and cyclooctyl. R$^4$ may also be hydrogen. Methyl is the most preferred R$^3$ and R$^4$ groups. Each occurrence of z is 0 to 100 inclusive and each occurrence of w is 0 to 100 inclusive. Preferred values of z and w are 1 to 50 inclusive.

Specific examples of preferred unsaturated compounds useful in the process of the present invention include N,N-dimethylallyl amine, allyloxy-substituted polyethers, propylene, 1-butene, 1-hexene, styrene-vinylnorbornane, 5-vinylnorbornene, long-chain, linear alpha olefins such as 1-octadecene, internal olefins such as cyclopentene, cyclohexene, norbornene, and 3-hexene, branched olefins such as isobutylene and 3-methyl-1-octene, unsaturated polyolefins, e.g., polybutadiene, polyisoprene and EPDM, unsaturated acids or esters such as oleic acid, linoleic acid and methyl oleate, a vinyl siloxane of the Formula (XII), and combinations thereof, wherein Formula (XII) is

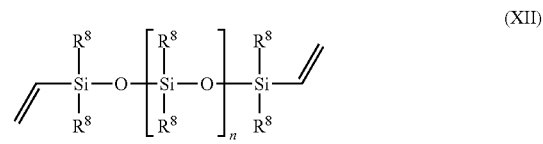

(XII)

wherein each occurrence of R$^8$ is independently a C1-C18 alkyl, C1-C18 substituted alkyl, vinyl, aryl, or a substituted aryl, and n is greater than or equal to zero. As defined herein, "internal olefin" means an olefin group not located at a chain or branch terminus, such as 3-hexene.

The silyl hydride employed in the reaction is not particularly limited. It can be any compound selected from the group consisting of R$_a$SiR$_{4-a}$, (RO)$_a$SiH$_{4-a}$, Q$_u$T$_v$T$_p^H$D$_w$D$^H{}_x$M$^H{}_y$M$_z$, and combinations thereof. The silyl hydride can contain linear, branched or cyclic structures, or combinations thereof. As used herein, each occurrence of R is independently C1-C18 alkyl, C1-C18 substituted alkyl, wherein R optionally contains at least one heteroatom, each occurrence of a independently has a value from 1 to 3, each of p, u, v, y and z independently has a value from 0 to 20, w and x are from 0 to 500, provided that p+x+y equals 1 to 500 and the valences of the all the elements in the silyl hydride are satisfied. Preferably, p, u, v, y, and z are from 0 to 10, w and x are from 0 to 100, wherein p+x+y equals 1 to 100.

As used herein, an "M" group represents a monofunctional group of formula R'$_3$SiO$_{1/2}$, a "D" group represents a difunctional group of formula R'$_2$SiO$_{2/2}$, a "T" group represents a trifunctional group of formula R'SiO$_{3/2}$, and a "Q" group represents a tetrafunctional group of formula SiO$_{4/2}$, an "M$^H$" group represents HR'$_2$SiO$_{1/2}$, a "T$^H$" represents HSiO$_{3/2}$, and a "D$^H$" group represents R'HSiO$_{2/2}$. Each occurrence of R' is independently C1-C18 alkyl, C1-C18 substituted alkyl, wherein R' optionally contains at least one heteroatom.

Examples of silyl hydrides containing at least one silylhydride functional group include R$_a$SiR$_{4-a}$, (RO)$_a$SiH$_{4-a}$, HSiR$_a$(OR)$_{3-a}$, R$_3$Si(CH$_2$)$_f$(SiR$_2$O)$_k$SiR$_2$H, (RO)$_3$Si(CH$_2$)$_f$(SiR$_2$O)$_k$ SiR$_2$H, Q$_u$T$_v$T$_p^H$D$_w$D$^H{}_x$M$^H{}_y$M$_z$, and combinations thereof, wherein Q is SiO$_{4/2}$, T is R'SiO$_{3/2}$, T$^H$ is HSiO$_{3/2}$, D is R'$_2$SiO$_{2/2}$, D$^H$ is R'HSiO$_{2/2}$, M$^H$ is HR'$_2$SiO$_{1/2}$, M is R'$_3$SiO$_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silyl hydride are satisfied. In the above formulations, p, u, v, y, and z may also be from 0 to 10, w and x may be from 0 to 100, wherein p+x+y equals 1 to 100.

Effective catalyst usage for dehydrogenative silylation ranges from 0.01 mole percent to 10 mole percent based on the molar quantity of the alkene to be reacted. Preferred levels are from 0.1 to 5 mole percent. Reaction may be run at temperatures from about 0° C. up to 300° C., depending on the thermal stability of the alkene, silyl hydride and the specific pyridine diimine complex. Temperatures in the range, 20-100° C., have been found to effective for most reactions.

Heating of reaction mixtures can be done using conventional methods as well as with microwave devices.

The dehydrogenative silylation reactions of this invention can be run at subatmospheric and supra-atmospheric pressures. Typically, pressures from about 1 atmosphere (0.1 MPa) to about 200 atmospheres (20 MPa), preferably to about 50 atmospheres (5.0 MPa), are suitable. Higher pressures are effective with volatile and/or less reactive alkenes which require confinement to enable high conversions.

A variety of reactors can be used in the process of this invention. Selection is determined by factors such as the volatility of the reagents and products. Continuously stirred batch reactors are conveniently used when the reagents are liquid at ambient and reaction temperature. These reactors can also be operated with a continuous input of reagents and continuous withdrawal of dehydrogenatively silylated reaction product.

With gaseous or volatile olefins and silanes, fluidized-bed reactors, fixed-bed reactors and autoclave reactors can be more appropriate. For example, in the synthesis of allyltrialkoxysilanes via the $(^{Mes}PDI)CoCH_3$-catalyzed dehydrogenative silylation of propene by trimethoxysilane or triethoxysilane (see Example 25), the cobalt pyridinediimine complex can be immobilized on a silica support and placed in a fixed-bed reactor. The mixture of propene and vaporized trialkoxysilane is then introduced at a flow rate and contact time effective to bring about the desired reaction at the selected pressure and temperature. Alternatively, the cobalt pyridinediimine catalyst can be placed in an autoclave reactor, or supported in a catalyst basket therein, and the reagents charged and maintained at the selected temperature and pressure to effect the dehydrogenative silylation.

In one embodiment, the silyl hydride has one of the following structures:

$R^1{}_a(R^2O)_bSiH$ (Formula XIII)

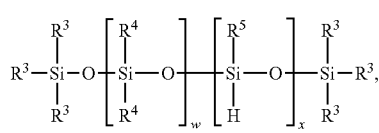
(Formula XIV)

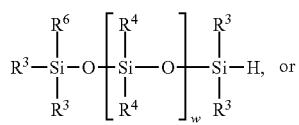
(Formula XV)

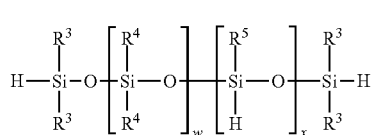
(Formula XVI)

wherein each occurrence of $R^1$, $R^2$, $R^3$, $R^4$, and $R^5$ is independently a C1-C18 alkyl, C1-C18 substituted alkyl, aryl, or substituted aryl, $R^6$ is hydrogen, a C1-C18 alkyl, C1-C18 substituted alkyl, aryl, or substituted aryl, x and w are independently greater than or equal to 0 (x is at least equal to 1 for Formula XIV)), and a and b are integers from 0 to 3 provided that a+b=3.

The catalysts of the invention are useful for catalyzing dehydrogenative silylation reactions. For example, when an appropriate silyl hydride, such as triethoxy silane, triethyl silane, $MD^HM$, or a silyl-hydride functional polysiloxane (SL 6020 from Momentive Performance Materials, Inc., for example) are reacted with a mono-unsaturated hydrocarbon, such as octene, dodecene, butene, etc, in the presence of the Co catalyst, the resulting product is a terminally-silyl-substituted alkene, where the unsaturation is in a beta position relative to the silyl group. A by-product of this reaction is the hydrogenated olefin. When the reaction is performed with a molar ratio of silane to olefin of 0.5:1, the resulting products are formed in a 1:1 ratio. An example is shown in the reaction scheme below.

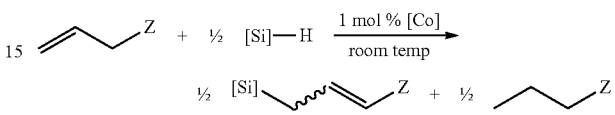

The reactions are typically facile at ambient temperatures and pressures, but can also be run at lower or higher temperatures (0 to 300° C.) or pressures (ambient to 205 atmospheres, (0.1-20.5 MPa)). A range of unsaturated compounds can be used in this reaction, such as N,N-dimethylallyl amine, allyloxy-substituted polyethers, cyclohexene, and linear alpha olefins (i.e., 1-butene, 1-octene, 1-dodecene, etc.). When an alkene containing internal double bonds is used, the catalyst is capable of first isomerizing the olefin, with the resulting reaction product being the same as when the terminally-unsaturated alkene is used.

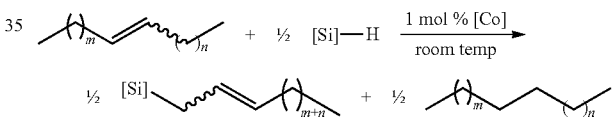

If the reaction is run with a 1:1 silyl-hydride to olefin ratio, the reaction can give a bis-substituted silane, where the silyl groups are in the terminal positions of the compound, and there is still an unsaturated group present in the product.

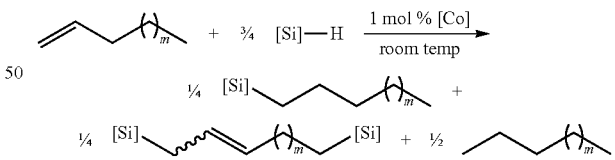

If the catalyst is first used to prepare a terminally-substituted silyl-alkene, a second silane may be added to produce an asymmetrically substituted bis-silyl alkene. The resulting silane is terminally substituted at both ends. This bis-silane can be a useful starting material for the production of alpha, omega-substituted alkanes or alkenes, such as diols and other compounds easily derived from the silylated product. Long chain alpha,omega-substituted alkanes or alkenes are not easily prepared today, and could have a variety of uses for preparing unique polymers (such as polyurethanes) or other useful compounds.

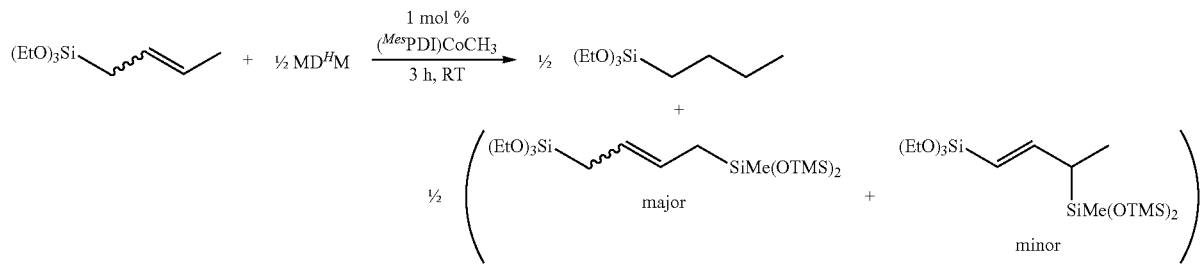

Because the double bond of an alkene is preserved during the dehydrogenative silylation reaction employing these cobalt catalysts, a singly-unsaturated olefin may be used to crosslink silyl-hydride containing polymers. For example, a silyl-hydride polysiloxane, such as SL6020 ($MD_{15}D^H{}_{30}M$), may be reacted with 1-octene in the presence of the cobalt catalysts of this invention to produce a crosslinked, elastomeric material. A variety of new materials can be produced by this method by varying the hydride polymer and length of the olefin used for the crosslinking. Accordingly, the catalysts used in the process of the invention have utility in the preparation of useful silicone products, including, but not limited to, coatings, for example release coatings, room temperature vulcanizates, sealants, adhesives, products for agricultural and personal care applications, and silicone surfactants for stabilizing polyurethane foams.

Furthermore, the dehydrogenative silylation may be carried out on any of a number of unsaturated polyolefins, such as polybutadiene, polyisoprene or EPDM-type copolymers, to either functionalize these commercially important polymers with silyl groups or crosslink them via the use of hydrosiloxanes containing multiple SiH groups at lower temperatures than conventionally used. This offers the potential to extend the application of these already valuable materials in newer commercially useful areas.

In one embodiment, the catalysts are useful for dehydrogenative silylation of a composition containing a silyl hydride and a compound having at least one unsaturated group. The process includes contacting the composition with a metal complex of the catalyst, either supported or unsupported, to cause the silyl hydride to react with the compound having at least one unsaturated group to produce a dehydrogenative silylation product, which may contain the metal complex catalyst. The dehydrogenative silylation reaction can be conducted optionally in the presence of a solvent. If desired, when the dehydrogenative silylation reaction is completed, the metal complex can be removed from the reaction product by magnetic separation and/or filtration. These reactions may be performed neat, or diluted in an appropriate solvent. Typical solvents include benzene, toluene, diethyl ether, etc. It is preferred that the reaction is performed under an inert atmosphere. The catalyst can be generated in-situ by reduction using an appropriate reducing agent.

The catalyst complexes of the invention are efficient and selective in catalyzing dehydrogenative silylation reactions. For example, when the catalyst complexes of the invention are employed in the dehydrogenative silylation of an alkyl-capped allyl polyether or a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. Further, when the compound containing an unsaturated group is an unsaturated amine compound, the dehydrogenatively silylated product is essentially free of internal addition products and isomerization products of the unsaturated amine compound. As used herein, "essentially free" is meant no more than 10 wt %, preferably 5 wt % based on the total weight of the hydrosilylation product. "Essentially free of internal addition products" is meant that silicon is added to the terminal carbon.

The following examples are intended to illustrate, but in no way limit the scope of the present invention. All parts and percentages are by weight and all temperatures are in degrees Celsius unless explicitly stated otherwise. All the publications and the US patents referred to in the application are hereby incorporated by reference in their entireties.

EXAMPLES

General Considerations

All air- and moisture-sensitive manipulations were carried out using standard vacuum line, Schlenk, and cannula techniques or in an MBraun inert atmosphere dry box containing an atmosphere of purified nitrogen. Solvents for air- and moisture-sensitive manipulations were initially dried and deoxygenated using literature procedures (Pangborn, A B et al., Organometallics 15:1518 (1996)). Chloroform-d and benzene-$d_6$ were purchased from Cambridge Isotope Laboratories. The complexes ($^{iPr}$PDI)CoN$_2$, (Bowman A C et al., JACS 132:1676 ($^{2010}$)), ($^{Et}$PDI)CoN$_2$, (Bowman A C et al., JACS 132:1676 (2010)), ($^{iPr}$BPDI)CoN$_2$, (Bowman A C et al., JACS 132:1676 (2010)), ($^{Mes}$PDI)CoCH$_3$, (Humphries, M J Organometallics 24:2039.2 (2005)), ($^{Mes}$PDI)CoCl, (Humphries, M J Organometallics 24:2039.2 (2005)) were prepared according to reported literature procedures. Bis(trimethylsiloxy)methylsilane $MD^HM$ (EtO)$_3$SiH and Et$_3$SiH were acquired from Momentive Performance Materials and were distilled from calcium hydride before use. The substrates, 1-octene (TCI America), tert-butylethylene or TBE (Alfa Aesar), N,N-dimethylallylamine (TCI America) and styrene (Alfa Aesar) were dried on calcium hydride and distilled under reduced pressure before use. 1-Butene (TCI America), allylamine (Alfa Aesar) and allylisocyanate (Alfa Aesar) were dried over 4 Å molecular sieves. SilForce® SL6100 ($M^{vi}D_{120}M^{vi}$), SilForce® SL6020 ($MD_{15}D^H{}_{30}M$) and the allyl polyethers were acquired from Momentive Performance Materials and dried under high vacuum for 12 hours before use.

For liquid samples, $^1$H NMR spectra were recorded on Inova 400 and 500 spectrometers operating at 399.78, and 500.62 MHz, respectively. $^{13}$C NMR spectra were recorded on an Inova 500 spectrometer operating at 125.893 MHz. All $^1$H and $^{13}$C NMR chemical shifts are reported relative to SiMe$_4$ using the $^1$H (residual) and $^{13}$C chemical shifts of the solvent as a secondary standard. The following abbreviations and terms are used: bs—broad singlet; s—singlet; t—triplet; bm—broad multiplet; GC—Gas Chromatography; MS—Mass Spectroscopy; THF—tetrahydrofuran GC analyses were performed using a Shimadzu GC-2010 gas chromatograph equipped with a Shimadzu AOC-20s autosampler and a Shimadzu SHRXI-5MS capillary column (15m×250 μm). The instrument was set to an injection volume of 1 μL, an inlet split ratio of 20:1, and inlet and detector temperatures of 250° C. and 275° C., respectively. UHP-grade helium was used as carrier gas with a flow rate of 1.82 mL/min. The temperature program used for all the analyses is as follows: 60° C., 1 min; 15° C./min to 250° C., 2 min.

Catalyst loadings in the following text are reported in mol % of the cobalt complex ($mol_{Co\ complex}/mol_{olefin} \times 100$).

Example 1

Synthesis of ($^{Mes}$PDI)CoN$_2$

This compound was prepared in a manner similar to the synthesis of ($^{Mes}$PDI)CoN$_2$ (Bowman, supra) with 0.500 g (0.948 mmol) of ($^{Mes}$PDI)CoCl$_2$, 0.110 g (4.75 mmol, 5.05 equiv) of sodium and 22.0 g (108 mmol, 114 equiv) of mercury. Recrystallization from 3:1 pentane/toluene yielded 0.321 g (70%) of very dark teal crystals identified as ($^{Mes}$PDI)CoN$_2$. Analysis for $C_{27}H_{31}N_5Co$: Calc. C, 66.93; H, 6.45; N, 14.45. Found. C, 66.65; H, 6.88; N, 14.59. $^1$H NMR (benzene-d$_6$): 3.58 (15 Hz), 4.92 (460 Hz). IR (benzene): $\upsilon_{NN}$=2089 cm$^1$.

Example 2

Synthesis of ($^{Mes}$PDI)CoOH

A 20 mL scintillation vial was charged with 0.100 g (0.203 mmol) of ($^{Mes}$PDI)CoCl, 0.012 g (0.30 mmol, 1.5 equiv) of NaOH, and approximately 10 mL THF. The reaction was stirred for two days upon which the color of the solution changed from dark pink to red. THF was removed in vacuo and the residue was dissolved in approximately 20 mL toluene. The resulting solution was filtered through Celite and the solvent was removed from the filtrate in vacuo. Recrystallization of the crude product from 3:1 pentane/toluene yielded 0.087 g (90%) of dark pink crystals identified as ($^{Mes}$PDI)CoOH. The compound is dichroic in solution exhibiting a pink color with a green hue. Analysis for $C_{27}H_{32}CoN_3O$: Calc. C, 68.49; H, 6.81; N, 8.87. Found. C, 68.40; H, 7.04; N, 8.77. $^1$H NMR (benzene-d$_6$):): δ=0.26 (s, 6H, C(CH$_3$)), 1.07 (s, 1H, CoOH), 2.10 (s, 12H, o-CH$_3$), 2.16 (s, 6H, p-CH$_3$), 6.85 (s, 4H, m-aryl), 7.49 (d, 2H, m-pyridine), 8.78 (t, 1H, p-pyridine). $^{13}$C {$^1$H} NMR (benzene-d$_6$): δ=19.13 (o-CH$_3$), 19.42 (C(CH$_3$)), 21.20 (p-CH$_3$) 114.74 (p-pyridine), 121.96 (m-pyridine), 129.22 (m-aryl), 130.71 (o-aryl), 134.78 (p-aryl), 149.14 (i-aryl), 153.55 (o-pyridine), 160.78 (C=N). IR (benzene): $\upsilon_{OH}$=3582 cm$^{-1}$.

Example 3

Silylation of 1-Octene with MD$^H$M Using Various Co Complexes

In a nitrogen-filled drybox, a scintillation vial was charged with 0.100 g (0.891 mmol) of 1-octene and 0.009 mmol (1 mol %) of the cobalt complex (see Table 1 for specific amounts). 0.100 g (0.449 mmol, 0.50 equiv) of MD$^H$M was then added to the mixture and the reaction was stirred at room temperature for one hour. The reaction was quenched by exposure to air and the product mixture was analyzed by gas chromatography and NMR spectroscopy.

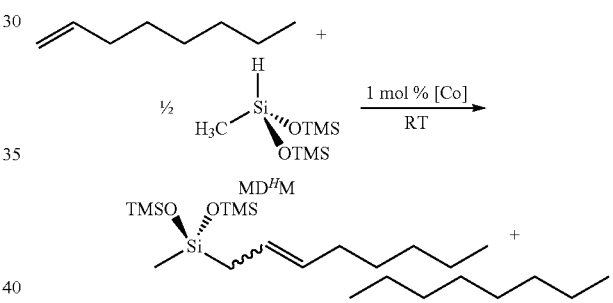

TABLE 1

| | Catalyst screening for the silylation of 1-octene with MD$^H$M.* | | | | | | |
|---|---|---|---|---|---|---|---|
| | | | 1 hr | | | 24 hrs | |
| Catalyst | | Amount | % conv | % silylated pdt | % octane | % conv | % silylated pdt | % octane |
| 3A | 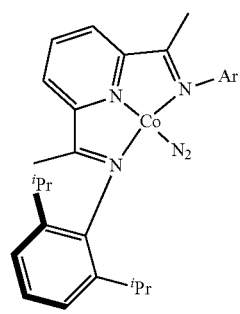 | 5 mg (0.009 mmol) | Trace | — | — | 39 | 19 | 20 |

TABLE 1-continued

Catalyst screening for the silylation of 1-octene with MD$^H$M.*

| Catalyst | | Amount | 1 hr | | | 24 hrs | | |
|---|---|---|---|---|---|---|---|---|
| | | | % conv | % silylated pdt | % octane | % conv | % silylated pdt | % octane |
| 3B | | 6 mg (0.009 mmol) | Trace | — | — | 46 | 23 | 23 |
| 3C | | 4 mg (0.008 mmol) | 87 | 47 | 40 | >98 | 52 | 46 |
| 3D | | 4 mg (0.008 mmol) | >98 | 46 | 52 | — | — | — |
| 3E | | 4 mg (0.008 mmol) | >98 | 49 | 49 | — | — | — |

TABLE 1-continued

Catalyst screening for the silylation of 1-octene with MD$^H$M.*

| | | | 1 hr | | | 24 hrs | |
| Catalyst | | Amount | % conv | % silylated pdt | % octane | % conv | % silylated pdt | % octane |
|---|---|---|---|---|---|---|---|---|
| 3F | 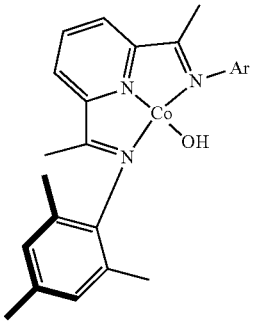 | 4 mg (0.008 mmol) | 65 | 35 | 30 | >98 | 49 | 49 |

*% Conversion and product distribution determined by GC-FID. % octane and % silylated product are reported as percentages of the compounds in the reaction mixture.

Example 4

Silylation of 1-Octene with Different Silanes Using ($^{Mes}$PDI)CoCH$_3$ and ($^{Mes}$PDI)CoN$_2$ In a nitrogen-filled drybox, a scintillation vial was charged with 0.100 g (0.891 mmol) of 1-octene and 0.009 mmol (1 mol %) of the cobalt complex [0.004 g ($^{Mes}$PDI)CoCH$_3$ or 0.004 g ($^{Mes}$PDI)CoN$_2$]. 0.449 mmol (0.5 equiv) of the silane (0.100 g MD$^H$M, 0.075 g (EtO)$_3$SiH or 0.052 g Et$_3$SiH) was then added to the mixture and the reaction was stirred at room temperature for the desired amount of time. The reaction was quenched by exposure to air and the product mixture was analyzed by gas chromatography and NMR spectroscopy. Results are shown in Table 2.

TABLE 2

Silylation of 1-octene with various silanes.*

| Catalyst | Silane | Time | % conv | % silylated pdt | % octane |
|---|---|---|---|---|---|
| 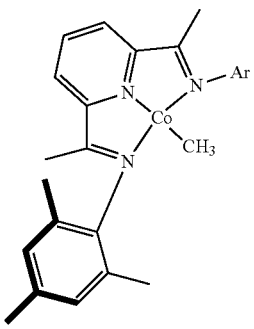 | MD$^H$M | 15 min | >98 | 49 | 49 |
| | (EtO)$_3$SiH | 15 min | >98 | 43 | 55 |
| | Et$_3$SiH | 24 hrs | >98 | 46 | 52 |
| 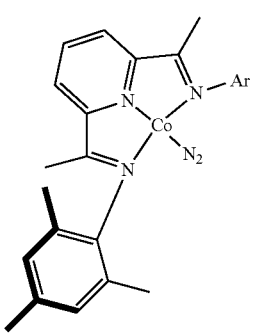 | MD$^H$M | 30 min | >98 | 46 | 52 |
| | (EtO)$_3$SiH | 15 min | >98 | 45 | 53 |
| | Et$_3$SiH | 24 hrs | 88 | 45 | 43 |

*% Conversion and product distribution determined by GC-FID. % octane and % silylated product are reported as percentages of the compounds in the reaction mixture.

Example 5

In Situ Activation of Cobalt Pre-Catalysts

A 20 mL scintillation vial was charged with 0.100 g (0.891 mmol) of 1-octene, 0.100 g (0.449 mmol) MD$^H$M and 0.005 g (0.009 mmol, 1 mol %) of ($^{Mes}$PDI)CoCl$_2$. 0.019 mmol (2 mol %) of the activator (0.019 mL of 1.0 M NaHBEt$_3$ in toluene; 0.012 mL of 1.6 M CH$_3$Li in diethyl ether; 0.019 mL of 1.0 M DIBAL-H in toluene; 0.003 g LiHMDS) was then added to the mixture and the reaction was stirred for 1 hour at room temperature. The reaction was quenched by exposure to air followed by analysis of the mixture by GC. In all cases, full conversion of 1-octene to an approximately 1:1 mixture of 1-bis(trimethylsiloxy)methylsilyl-2-octene and octane was observed.

Example 6

Silylation of Cis- and Trans-4-Octene with Different Silanes Using ($^{Mes}$PDI)CoCH$_3$ The reactions were carried out in a manner similar to silylation of 1-octene using 0.100 g (0.891 mmol) of cis- or trans-4-octene and 0.009 mmol (1 mol %) of the cobalt complex (0.004 g of ($^{Mes}$PDI)CoCH$_3$), and 0.629 mmol (0.5 equiv) of the silane (0.100 g MD$^H$M, 0.075 g (EtO)$_3$SiH or 0.052 g Et$_3$SiH). The reactions were stirred at room temperature for 24 hours and then quenched by exposure to air and the product mixtures were analyzed by gas chromatography and NMR spectroscopy. Results are shown in Table 3.

TABLE 3

Silylation of cis- and trans-4-octene with various silanes.*

| Olefin | Silane | % conv | % silylated pdt** | % octane |
|---|---|---|---|---|
| cis-4-octene | MD$^H$M | >98 | 51 (88% C$_1$) | 47 |
| | (EtO)$_3$SiH | | intractable mixture | |
| | Et$_3$SiH | 70 | 35 (75% C$_1$) | 35 |
| trans-4-octene | MD$^H$M | >98 | 53 (93% C$_1$) | 45 |
| | (EtO)$_3$SiH | | intractable mixture | |
| | Et$_3$SiH | 85 | 39 (72% C$_1$) | 46 |

*% Conversion and product distribution determined by GC-FID. % octane and % silylated product are reported as percentages of the compounds in the reaction mixture.
**Values in parentheses are % 1-silyl-2-octene product.

Example 7

Silylation of 1-Octene with MD$^H$M Using ($^{Mes}$PDI)CoCH$_3$ in the Presence of H$_2$ In a nitrogen-filled drybox, a thick-walled glass vessel was charged with 0.200 g (1.78 mmol) of 1-octene and 0.400 g (1.80 mmol) of MD$^H$M. The solution was frozen in the cold well and 0.008 g (0.017 mmol, 1 mol %) of ($^{Mes}$PDI)CoCH$_3$ was added on the surface of the frozen solution. The reaction vessel was quickly capped, brought out of the drybox and placed in a Dewar filled with liquid nitrogen to keep the solution frozen. The vessel was degassed and approximately 1 atm of H$_2$ was admitted. The solution was thawed and stirred at room temperature for one hour. The reaction was quenched by opening the glass vessel to air. Analysis of the product mixture by GC showed >98% conversion of 1-octene to octane (74%) and 1-bis(trimethylsiloxy)methylsiloctane (24%).

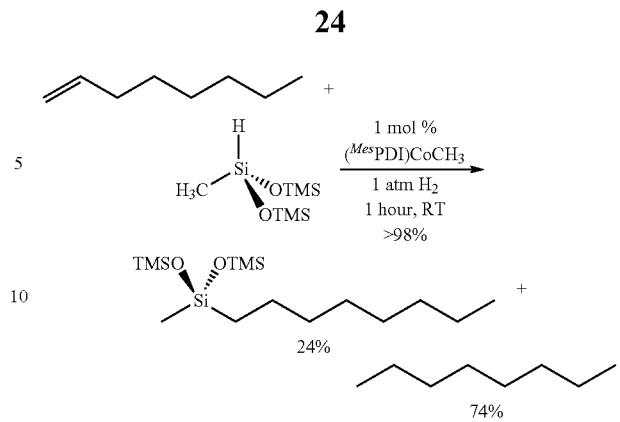

Characterization of Products

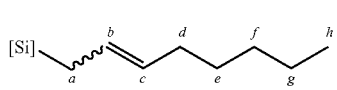

1-bis(trimethylsiloxy)methylsilyl-2-octene $^1$H NMR (benzene-d$_6$): δ=0.16 (s, 3H, (OTMS)$_2$SiCH$_3$), 0.18 (s, 18H, OSi(CH$_3$)$_3$), 0.90 (t, 3H, H$^h$), 1.27 (m, 2H, H$^f$), 1.29 (m, 2H, H$^g$), 1.40 (m, 2H, H$^e$), 1.59 (d, 2H {75%}, H$^a$—trans isomer), 1.66 (d, 2H {25%}, H$^a$—cis isomer), 2.07 (m, 2H {75%}, H$^d$—trans isomer), 2.11 (m, 2H {25%}, H$^d$—cis isomer), 5.44 (m, 1H {75%}, H$^e$—trans isomer), 5.48 (m, 1H {25%}, H$^e$—cis isomer), 5.55 (m, 1H {75%}, H$^b$—trans isomer), 5.60 (m, 1H {25%}, H$^b$—cis isomer). $^{13}$C{$^1$H} NMR (benzene-d$_6$): δ=−0.46 ((OTMS)$_2$SiCH$_3$), 2.04 (OSi(CH$_3$)$_3$), 14.35 (C$^h$), 22.99 (C$^g$-trans), 23.05 (C$^g$-cis), 24.12 (C$^a$), 29.87 (C$^e$—cis), 30.00 (C$^e$—trans), 31.79 (C$^f$—trans), 32.05 (C$^f$—cis), 33.37 (C$^d$), 124.37 (C$^b$—cis), 125.14 (C$^b$—trans), 129.06 (C$^c$—cis), 130.47 (C$^c$—trans).

1-triethoxysilyl-2-octene $^1$H NMR (benzene-d$_6$): δ=0.88 (t, 3H, H$^h$), 1.19 (t, 9H, OCH$_2$CH$_3$), 1.26 (m, 2H, H$^f$), 1.26 (m, 2H, H$^g$), 1.36 (m, 2H, H$^e$), 1.74 (d, 2H {75%}, H$^a$—trans isomer), 1.78 (d, 2H {25%}, H$^a$—cis isomer), 2.02 (m, 2H {75%}, H$^d$—trans isomer), 2.13 (m, 2H {25%}, H$^d$—cis isomer), 3.83 (q, 6H, OCH$_2$CH$_3$) 5.45 (m, 1H {75%}, H$^e$—trans isomer), 5.49 (m, 1H {25%}, H$^e$—cis isomer), 5.66 (m, 1H {75%}, H$^b$—trans isomer), 5.69 (m, 1H {25%}, H$^b$—cis isomer). $^{13}$C{$^1$H} NMR (benzene-d$_6$): δ=14.35 (C$^h$), 17.14 (C$^a$), 18.61 (OCH$_2$CH$_3$), 22.98 (C$^g$), 17.14 (C$^a$), 29.87 (C$^e$), 31.72 (C$^f$), 33.26 (C$^d$—trans), 33.47 (C$^d$—cis), 58.69 (OCH$_2$CH$_3$), 123.38 (C$^b$—cis), 124.26 (C$^b$—trans), 130.94 (C$^c$—trans), 130.98 (C$^c$—cis).

1-triethylsilyl-2-octene $^1$H NMR (benzene-d$_6$): δ=0.55 (t, 6H, Si(CH$_2$CH$_3$)$_3$), 0.91 (t, 3H, H$^h$), 0.97 (t, 9H, Si(CH$_2$CH$_3$)$_3$), 1.28 (m, 2H, H$^f$), 1.32 (m, 2H, H$^g$), 1.36 (m, 2H, H$^e$), 1.50 (d, 2H {75%}, H$^a$—trans isomer), 1.54 (d, 2H {25%}, H$^a$—cis isomer), 2.03 (m, 2H {75%}, H$^d$—trans isomer), 2.08 (m, 2H {25%}, H$^d$—cis isomer), 5.47 (m, 1H {75%}, H$^e$—trans isomer), 5.50 (m, 1H {25%}, H$^e$—cis isomer), 5.36 (m, 1H {75%}, H$^b$—trans isomer), 5.38 (m, 1H {25%}, $H^b$—cis isomer). $^{13}C$ {$^1H$} NMR (benzene-$d_6$): δ=2.82 (Si(CH$_2$CH$_3$)$_3$), 7.70 (Si(CH$_2$CH$_3$)$_3$), 14.42 ($C^h$), 17.70 ($C^a$-trans), 17.71 ($C^a$—cis), 23.04 ($C^g$), 23.19 ($C^e$), 29.24 ($C^f$), 32.40 ($C^d$—trans), 32.47 ($C^d$—cis), 126.41 ($C^b$—trans), 126.46 ($C^b$—cis), 129.31 ($C^c$—trans), 129.33 ($C^c$—cis).

Example 8

Silylation of 1-Butene with Different Silanes Using ($^{Mes}$PDI)CoCH$_3$

A thick-walled glass vessel was charged with 0.449 mmol of the silane (0.100 g MD'M, 0.075 g (EtO)$_3$SiH or 0.052 g Et$_3$SiH) and 0.004 g (0.009 mmol) of ($^{Mes}$PDI)CoCH$_3$. The mixture was frozen in liquid nitrogen and the reaction vessel was degassed. 0.891 mmol of 1-butene was admitted into the vessel using a calibrated gas bulb. The mixture was thawed and stirred at room temperature for 1 hour. The volatiles were distilled into a J. Young tube containing CDCl$_3$ and analyzed by NMR spectroscopy. The remaining residue was exposed to air and analyzed by GC and NMR spectroscopy. Results are shown in Table 4.

TABLE 4

Silylation of 1-butene with various silanes.*

| Catalyst | Silane | % conv | cis isomer | trans isomer | Volatiles |
|---|---|---|---|---|---|
| | MD$^H$M | >95 | 52 | 48 | butane |
| | (EtO)$_3$SiH | >95 | 32 | 68 | butane |
| | Et$_3$SiH | <5 | — | — | 1-butene |

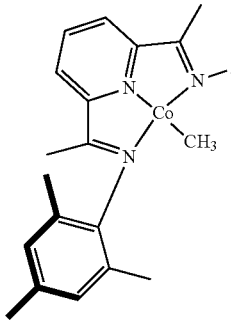

*% Conversion and product distribution determined by GC and $^1$H NMR spectroscopy.

Characterization of Products

1-bis(trimethylsiloxy)methylsilyl-2-butene $^1$H NMR (CDCl$_3$): δ=0.00 and 0.01 (s, 2×3H, (OTMS)$_2$SiCH$_3$), 0.08 and 0.09 (s, 2×18H, OSi(CH$_3$)$_3$), 1.38 and 1.45 (d, 2×2H, SiCH$_2$CH═CH), 1.57 and 1.64 (d, 2×3H, CH═CHCH$_3$), 5.25 to 5.43 (m, 4×1H, CH═CH). $^{13}$C {$^1$H} NMR (CDCl$_3$): δ=−0.44 and −0.60 ((OTMS)$_2$SiCH$_3$); 1.98 (OSi(CH$_3$)$_3$); 18.27 (CH═CHCH$_3$); 19.19 and 23.71 (SiCH$_2$CH═CH); 122.17, 124.12, 125.34, 126.09 (CH═CH).

1-triethoxysilyl-2-butene $^1$H NMR (CDCl$_3$): δ=1.21 (t, 2×9H, OCH$_2$CH$_3$), 1.55 and 1.60 (d, 2×2H, SiCH$_2$CH═CH), 1.61 and 1.62 (d, 2×3H, CH═CHCH$_3$), 3.81 and 3.82 (q, 2×6H, OCH$_2$CH$_3$), 5.38 to 5.48 (m, 4×1H, CH═CH). $^{13}$C {$^1$H} NMR (CDCl$_3$): δ=11.84 (SiCH$_2$CH═CH); 18.20 and 18.23 (CH═CHCH$_3$); 18.36 and 18.38 (OCH$_2$CH$_3$); 58.64 and 58.65 (OCH$_2$CH$_3$); 123.33, 123.68, 124.46, 125.31 (CH═CH).

Example 9

Silylation of TBE (Tert-Butyl Ethylene) with MD$^H$M Using ($^{Mes}$PDI)CoCH$_3$ This reaction was carried out in a manner similar to the silylation of 1-butene using 0.100 g (0.449 mmol) of MD$^H$M, 0.004 g (0.009 mmol) of ($^{Mes}$PDI)CoCH$_3$ and 0.891 mmol of TBE. Analysis of the volatiles by $^1$H NMR spectroscopy showed a 4:1 mixture of unreacted TBE and 2,2-dimethylbutane (33% conversion). Analysis of the silane product by GC and NMR spectroscopy showed only trans-1-bis(trimethylsiloxy)methylsilyl-3,3-dimethyl-1-butene. $^1$H NMR (CDCl$_3$): δ= 0.00 (s, 3H, (OTMS)$_2$SiCH$_3$), 0.09 (s, 18H, OSi(CH$_3$)$_3$), 0.99 (s, 9H, C(CH$_3$)$_3$), 5.37 (d, J=19.07, 1H SiCH═CH), 6.13 (d, J=19.07 Hz, 1H, CH═CHC(CH$_3$)$_3$). $^{13}$C {$^1$H} NMR (CDCl$_3$): δ=0.00 ((OTMS)$_2$SiCH$_3$); 2.01 (OSi(CH$_3$)$_3$); 28.96 (C(CH$_3$)$_3$); 34.91 (C(CH$_3$)$_3$); 121.01 (SiCH═CH); 159.23 (SiCH═CH).

Example 10

Silylation of N,N-Dimethylallylamine with Different Silanes Using ($^{Mes}$PDI)CoCH$_3$ and ($^{Mes}$PDI)CoN$_2$ In a nitrogen-filled drybox, a scintillation vial was charged with 0.090 g (1.1 mmol) of N,N-dimethylallylamine and 0.5 mmol (0.5 equiv) of the silane (0.118 g MD$^H$M, 0.087 g (EtO)$_3$SiH or 0.062 g Et$_3$SiH). 0.01 mmol (1 mol %) of the cobalt complex [0.005 g ($^{Mes}$PDI)CoCH$_3$ or 0.005 g ($^{Mes}$PDI)CoN$_2$] was then added and the reaction was stirred for one hour at room temperature. The reaction was quenched by exposure to air and the product mixture was analyzed by NMR spectroscopy. Results are shown in Table 5.

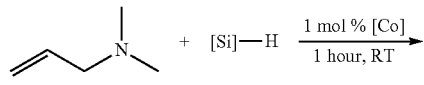

-continued

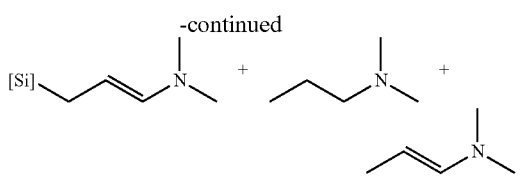

N(CH$_3$)$_2$), 3.84 (q, J=7.0, 6H, OCH$_2$CH$_3$), 4.31 (dt, J=13.6, 7.5 Hz, 1H, CH$_2$CH=CH), 5.85 (dt, J=13.6, 1.2 Hz, 1H, CH$_2$CH=CH). $^{13}$C {$^1$H} NMR (benzene-d$_6$): δ=13.48 (SiCH$_2$CH=CH), 18.41 (OCH$_2$CH$_3$), 40.98 (N(CH$_3$)$_2$), 58.65 (OCH$_2$CH$_3$), 92.95 (CH$_2$CH=CH), 140.82 (CH$_2$CH=CH).

TABLE 5

Silylation of N,N-dimethylallylamine with various silanes.*

| Catalyst | Silane | % conv | [Si]⌒⌒N | ⌒⌒N | ⌒=⌒N |
|---|---|---|---|---|---|
| (structure 1) | MD$^H$M | >95 | 53 | 42 | Trace |
| | (EtO)$_3$SiH | >95 | 47 | 47 | Trace |
| | Et$_3$SiH | <5 | — | — | — |
| (structure 2) | MD$^H$M | >95 | 38 | 28 | 29 |
| | (EtO)$_3$SiH | >95 | 45 | 50 | Trace |
| | Et$_3$SiH | 65 | — | — | 65 |

*% Conversion and product distribution determined by $^1$H NMR spectroscopy.

Characterization of Products

N,N-dimethyl-3-bis(trimethylsiloxy)methylsilyl-1-propenylamine $^1$H NMR (benzene-d$_6$): δ=0.14 (s, 3H, (OTMS)$_2$SiCH$_3$), 0.18 (s, 18H, OSi(CH$_3$)$_3$), 1.50 (dd, J=7.7, 1.2 Hz, 2H, SiCH$_2$CH=CH), 2.35 (s, 6H, N(CH$_3$)$_2$), 4.25 (dt, J=13.6, 7.7 Hz, 1H, CH$_2$CH=CH), 5.80 (dt, J=13.6, 1.2 Hz, 1H, CH$_2$CH=CH). $^{13}$C {$^1$H} NMR (benzene-d$_6$): δ=0.61 ((OTMS)$_2$SiCH$_3$), 2.12 (OSi(CH$_3$)$_3$), 20.49 (SiCH$_2$CH=CH), 41.08 (N(CH$_3$)$_2$), 94.09 (CH$_2$CH=CH), 140.57 (CH$_2$CH=CH).

N,N-dimethyl-3-triethoxysilyl-1-propenylamine $^1$H NMR (benzene-d$_6$): δ=1.18 (t, J=7.0, 9H, OCH$_2$CH$_3$), 1.66 (dd, J=7.5, 1.2 Hz, 2H, SiCH$_2$CH=CH), 2.30 (s, 6H, Example 11

Silylation of Methyl Capped Allyl Polyether (H$_2$C=CHCH$_2$O(C$_2$H$_4$O)$_{8.9}$CH$_3$) with Methylbis(Trimethylsilyloxy)Silane (MD$^H$M)

A scintillation vial was charged with 0.100 g of methyl capped allyl polyether having an average formula of H$_2$C=CHCH$_2$O(C$_2$H$_4$O)$_{8.9}$CH$_3$ (0.215 mmol) and 0.025 g (0.11 mmol, 0.5 equiv) of MD'M. To the stirring solution of polyether and silane was added 1 mg (0.002 mmol; 1 mol %) of ($^{Mes}$PDI)CoCH$_3$. The scintillation vial was sealed and removed from the drybox and placed in a 65° C. oil bath. The reaction mixture was stirred for 1 hour after which the vial was removed from the oil bath and the reaction was quenched by opening the vessel to air. Analysis of $^1$H NMR spectrum of the product established a 1:1 mixture of silylated product and propylpolyether.

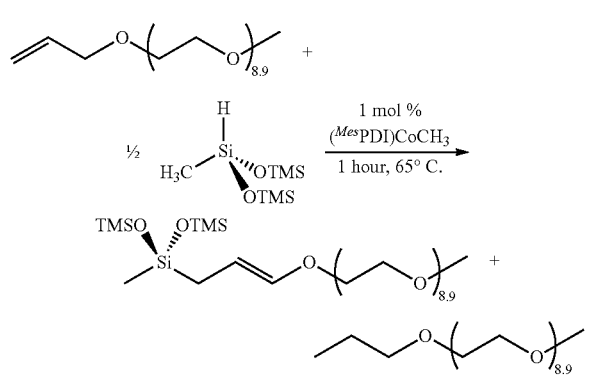

$(OTMS)_2Si(CH_3)CH_2CH=CHO(C_2H_4O)_{8.9}CH_3$. $^1$H NMR (CDCl$_3$): δ=−0.06 (s, 3H, (OTMS)$_2$SiCH$_3$), 0.03 (s, 18H, OSi(CH$_3$)$_3$), 1.55 (dd, J=7.8, 1.1 Hz, 2H, SiCH$_2$CH=CH), 3.32 (s, 3H, OCH$_3$), 3.5-3.7 (O—CH$_2$CH$_2$—O), 5.28 (dt, J=18.5, 1.1 Hz, 1H, CH$_2$CH=CH), 6.07 (dt, J=18.5, 7.8 Hz, 1H, CH$_2$CH=CH). $^{13}$C {$^1$H} NMR (CDCl$_3$): δ=0.11 ((OTMS)$_2$SiCH$_3$), 1.65 (OSi(CH$_3$)$_3$), 29.24 (SiCH$_2$CH=CH), 59.00 (OCH$_3$), 70-72 (O—CH$_2$CH$_2$—O), 127.02 (CH$_2$CH=CH), 144.38 (CH$_2$CH=CH).

Example 12

Crosslinking of M$^{vi}$D$_{120}$M$^{vi}$ (SL 6100) and MD$_{15}$D$^H_{30}$M (SL 6020) at Room Temperature A scintillation vial was charged with 1.0 g of M$^{vi}$D$_{120}$M$^{vi}$ (SL 6100) in which M$^{vi}$ is vinyl dimethyl SiO, and 0.044 g of MD$_{15}$D$^H_{30}$M (SL 6020). In a second vial, a solution of the catalyst was prepared by dissolving 0.010 g of ($^{Mes}$PDI)CoCH$_3$ or ($^{Mes}$PDI)CoN$_2$ in approximately 0.300 g of toluene. The catalyst solution was added to a stirring solution of SL 6100 and SL 6020 and the reaction was monitored for gel formation. The resulting gel after quenching the reaction by exposure to air was softer than that obtained from the same reaction using Karstedt's compound as catalyst.

Polymer crosslinking under neat conditions was also investigated by adding 0.010 g of ($^{Mes}$PDI)CoCH$_3$ or ($^{Mes}$PDI)CoN$_2$ to a stirring solution of 1.0 g SL 6100 and 0.044 g SL 6020. Soft gels were also obtained from these reactions.

Example 13

Crosslinking of M$^{vi}$D$_{120}$M$^{vi}$ (SL 6100) and MD$_{15}$D$^H_{30}$M (SL 6020) at 65° C.

These reactions were carried out in a manner similar to those performed at room temperature, with the additional steps of sealing the scintillation vials, removing them from the drybox and placing them in a 65° C. oil bath. The resulting gels after quenching the reaction were indistinguishable from that obtained from the same reaction using Karstedt's compound as catalyst. Results are shown in Table 6.

TABLE 6

Gelation time for the crosslinking of SL 6100 and SL 6020 under various reaction conditions.

| Catalyst | Reaction Conditions | Gelation time | Quality of Gel | Color |
|---|---|---|---|---|
| (structure with CH$_3$) | RT, in toluene | 5 min | soft | dark yellow |
|  | RT, neat | 60 min | soft | light gray |
|  | 65° C., toluene | 5 min | hard | yellow |
|  | 65° C., neat | 15 min | hard | light yellow |
| (structure with N$_2$) | RT, in toluene | 20 min | soft | dark yellow |
|  | RT, neat | 60 min | soft | light gray |
|  | 65° C., toluene | 5 min | hard | yellow |
|  | 65° C., neat | 15 min | hard | light yellow |

Double Silylation Experiments

Example 14

Silylation of 1-bis(trimethylsiloxy)methylsilyl-2-octene with MD$^H$M Using ($^{Mes}$PDI)CoCH$_3$ This experiment was performed in a manner similar to the silylation of 1-octene using 0.100 g (0.301 mmol) of 1-bis(trimethylsiloxy)methylsilyl-2-octene, 0.034 g (0.152 mmol, 0.51 equiv) of MD'M, and 0.001 g (0.002 mmol, 1 mol %) of ($^{Mes}$PDI)CoCH$_3$. The reaction was stirred at room temperature for 24 hours and quenched by exposure to air. Analysis of the mixture by GC-FID, GC-MS and NMR spectroscopy showed an approximately 1:1 mixture of 1-bis(trimethylsiloxy)methylsilyloctane and 1,8-bis(bis(trimethylsiloxy)methylsilyl)-2-octene (major isomer).

Attempts to silylate 1-triethoxysilyl-2-octene with MD$^H$M yielded a mixture of disilylated products concomitant with the formation of 1-triethoxysilyloctane. Silylation of 1-bis(trimethylsiloxy)methylsilyl-2-octene and 1-triethoxysilyl-2-octene with TES under the same conditions yielded only the hydrogenated products, 1-bis(trimethylsiloxy)methylsilyloctane and 1-triethoxysilyloctane, respectively.

Example 15

Alternative Procedure for the Double Silylation of 1-Octene with MD$^H$M Using ($^{Mes}$PDI)CoCH$_3$ This experiment is performed in a manner similar to the silylation of 1-octene using 0.100 g (0.891 mmol) of 1-octene, 0.150 g (0.674 mmol, 0.756 equiv) of MD$^H$M and 0.004 g (0.008 mmol, 1 mol %) of ($^{Mes}$PDI)CoCH$_3$. The reaction was stirred at room temperature for 24 hours and quenched by exposure to air. Analysis of the mixture by GC-FID showed a 1:0.5:0.5 mixture of octane, 1-bis(trimethylsiloxy)methylsilyloctane and 1,8-bis(bis(trimethylsiloxy)methylsilyl)-2-octene (major isomer), respectively.

Example 16

Silylation of 1-Bis(Trimethylsiloxy)Methylsilyl-2-Butene with MD$^H$M Using ($^{Mes}$PDI)CoCH$_3$ This experiment was performed in a manner similar to the silylation of 1-bis(trimethylsiloxy)methylsilyl-2-octene using 0.100 g (0.361 mmol) of 1-bis(trimethylsiloxy)methylsilyl-2-butene, 0.040 g (0.18 mmol, 0.50 equiv) of MD$^H$M and 0.002 g (0.004 mmol, 1 mol %) of ($^{Mes}$PDI)CoCH$_3$. The reaction was stirred for 24 hours and quenched by exposure to air. Analysis of the mixture by NMR spectroscopy showed the following product distribution: 50% 1-bis(trimethylsiloxy)methylsilylbutane; 26% trans-1,4-bis(bis(trimethylsiloxy)-methylsilyl)-2-butene; 17% cis-1,4-bis(bis(trimethylsiloxy) methylsilyl)-2-butene; 5% trans-1,3-bis(bis(trimethylsiloxy) methylsilyl)-1-butene; and, 2% trans-1,4-bis(bis(trimethylsiloxy)methylsilyl)-1-butene.

Characterization of Products

1-bis(trimethylsiloxy)methylsilylbutane $^1$H NMR (CDCl$_3$): δ=0.01 (s, 3H, (OTMS)$_2$SiCH$_3$), 0.09 (s, 18H, OSi(CH$_3$)$_3$), 0.45 (m, 2H, SiCH$_2$CH$_2$CH$_2$CH$_3$), 0.88 (t, 3H, SiCH$_2$CH$_2$CH$_2$CH$_3$), 1.26-1.33 (m, 4H, SiCH$_2$CH$_2$CH$_2$CH$_3$). $^{13}$C {$^1$H} NMR (CDCl$_3$): δ=−0.66 ((OTMS)$_2$SiCH$_3$), 2.02 (OSi(CH$_3$)$_3$), 13.98 (SiCH$_2$CH$_2$CH$_2$CH$_3$), 17.46 (SiCH$_2$CH$_2$CH$_2$CH$_3$), 25.35 and 26.36 (SiCH$_2$CH$_2$CH$_2$CH$_3$).

Trans-1,4-bis(bis(trimethylsiloxy)methylsilyl)-2-butene $^1$H NMR (CDCl$_3$): δ=0.01 (s, 6H, (OTMS)$_2$SiCH$_3$), 0.09 (s, 36H, OSi(CH$_3$)$_3$), 1.39 (d, 4H, SiCH$_2$CH=CHCH$_2$Si), 5.21 (t, 2H, SiCH$_2$CH=CHCH$_2$Si). $^{13}$C {$^1$H} NMR (CDCl$_3$): δ=−0.66 ((OTMS)$_2$SiCH$_3$), 2.02 (OSi(CH$_3$)$_3$), 23.95 (SiCH$_2$CH=CHCH$_2$Si), 124.28 (SiCH$_2$CH=CHCH$_2$Si).

Cis-1,4-bis(bis(trimethylsiloxy)methylsilyl)-2-butene $^1$H NMR (CDCl$_3$): δ=0.01 (s, 6H, (OTMS)$_2$SiCH$_3$), 0.09 (s, 36H, OSi(CH$_3$)$_3$), 1.41 (d, 4H, SiCH$_2$CH=CHCH$_2$Si), 5.31 (t, 2H, SiCH$_2$CH=CHCH$_2$Si). $^{13}$C {$^1$H} NMR (CDCl$_3$): δ=−0.38 ((OTMS)$_2$SiCH$_3$), 2.01 (OSi(CH$_3$)$_3$), 19.12 (SiCH$_2$CH=CHCH$_2$Si), 122.86 (SiCH$_2$CH=CHCH$_2$Si).

Trans-1,3-bis(bis(trimethylsiloxy)methylsilyl)-1-butene $^1$H NMR (CDCl$_3$): δ=0.01 (s, 6H, (OTMS)$_2$SiCH$_3$), 0.09 (s, 36H, OSi(CH$_3$)$_3$), 1.04 (d, 3H, CHCH$_3$), 1.64 (m, 1H, CHCH$_3$), 5.28 (d, 1H, SiCH=CH), 6.27 (dd, 1H, SiCH=CH). $^{13}$C {$^1$H} NMR (CDCl$_3$): δ=−0.13 ((OTMS)$_2$SiCH$_3$), 2.00 (OSi(CH$_3$)$_3$), 12.07 (CHCH$_3$), 31.69 (CHCH$_3$), 123.37 (SiCH=CH), 151.01 (SiCH=CH).

Trans-1,4-bis(bis(trimethylsiloxy)methylsilyl)-1-butene $^1$H NMR (CDCl$_3$): δ=0.01 (s, 6H, (OTMS)$_2$SiCH$_3$), 0.09 (s, 36H, OSi(CH$_3$)$_3$), 0.58 (m, 2H, CH$_2$CH$_2$Si), 2.11 (m, 2H, CH$_2$CH$_2$Si), 5.46 (d, 1H, SiCH=CH), 6.20 (m, 1H, SiCH=CH). $^{13}$C {$^1$H} NMR (CDCl$_3$): δ=0.29 ((OTMS)$_2$SiCH$_3$), 2.07 (OSi(CH$_3$)$_3$), 16.28 (CH$_2$CH$_2$Si), 29.79 (CH$_2$CH$_2$Si), 125.73 (SiCH=CH), 151.52 (SiCH=CH).

Example 17

Synthesis of ($^{Mes}$PDI)Co-allyl

A 50 mL round-bottom flask was charged with 0.100 g (0.203 mmol) of ($^{Mes}$PDI)CoCl and approximately 20 mL of toluene. The pink solution was cooled in a liquid-nitrogen cooled cold well. 0.240 mL (0.240 mmol, 1.2 equiv) of a 1.0M allyl magnesium bromide in diethyl ether was then added dropwise to the cooled solution, and the reaction was stirred at room temperature for 3 hours. The solution was filtered through Celite, concentrated to approximately 1 mL and diluted with 3 mL pentane. Recrystallization of the crude product at −35° C. overnight yielded 0.083 g (0.17 mmol, 82%) of dark pink powder identified as ($^{Mes}$PDI)Co-allyl (Formula IV):

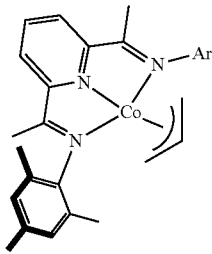

(Formula IV)

$^1$H NMR (C$_6$D$_6$): δ=1.61 (s, 6H, N=CCH$_3$), 1.79 (s, 12H, o-CH$_3$), 2.09 (s, 6H, p-CH$_3$), 5.23 (quintet, 1H, 10.4 Hz, allyl-CH), 6.71 (s, 4H, m-Ar), 7.42 (t, 7.5 Hz, 1H, p-py), 7.87 (d, 7.5 Hz, 2H, m-py). {$^1$H} $^{13}$C NMR(C$_6$D$_6$): δ=16.72 (N=CCH$_3$), 18.58 (o-CH$_3$), 21.04 (p-CH$_3$), 106.29 (allyl-CH), 115.42 (p-py), 120.48 (m-py), 129.20 (m-Ar), 130.36 (o-Ar), 134.17 (p-Ar), 147.31 (i-Ar), 149.94 (o-py), 167.85 (N=C); not found: allyl CH$_2$.

Example 18

Evaluation of the Catalytic Activity of ($^{Mes}$PDI)Co-Allyl

This experiment was performed in a scintillation vial using 0.100 g (0.891 mmol) of 1-octene, 0.100 g (0.449 mmol, 0.5 equiv) of MD$^H$M and 0.002 g (0.004 mmol, 1 mol %) of ($^{Mes}$PDI)Co-allyl. The reaction was monitored by GC and NMR spectroscopy and quenched prior to analysis via exposure to air. 95% conversion to product was achieved in 24 hours.

Example 19

Synthesis of ($^{Mes}$PDI)Co-benzyl

This experiment was performed in a manner similar to the synthesis of ($^{Mes}$PDI)Co-allyl using 0.100 g (0.203 mmol) of ($^{Mes}$PDI)CoCl and 0.026 g (0.20 mmol, 1 equiv) of benzyl potassium. The reaction was stirred at room temperature for 16 hours. Recrystallization of the crude product in 1:5 toluene/pentane at −35° C. overnight yielded 0.081 g (0.15 mmol, 73%) of navy blue powder identified as ($^{Mes}$PDI)Co-benzyl (Formula V):

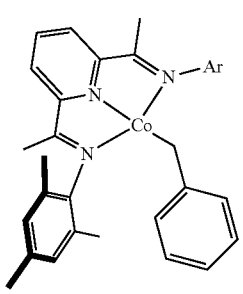

(Formula V)

Analysis for C$_{34}$H$_{38}$CoN$_3$: Calc. C, 74.57; H, 6.99; N, 7.67. Found C, 74.89; H, 7.14; N, 7.72. $^1$H NMR (C$_6$D$_6$): δ=−1.43 (s, 6H, N=CCH$_3$), 1.95 (s, 12H, o-CH$_3$), 2.35 (s, 6H, p-CH$_3$), 2.90 (s, 2H, CoCH$_2$Ph), 5.89 (d, 7.5 Hz, 2H, o-benzyl), 6.57 (pseudo t, 7.5 Hz, 2H, m-benzyl), 6.88 (t, 7.5 Hz, 1H, p-benzyl), 7.03 (s, 4H, m-Ar), 7.74 (d, 7.6 Hz, 2H, m-py), 10.41 (t, 7.6 Hz, 1H, p-py). {$^1$H} $^{13}$C NMR (C$_6$D$_6$): δ=3.60 (CoCH$_2$Ph), 19.11 (o-CH$_3$), 21.42 (p-CH$_3$), 24.81 (N=CCH$_3$), 117.14 (p-py), 119.70 (p-benzyl), 123.40 (m-py), 127.20 (o-benzyl), 127.27 (m-benzyl), 129.95 (m-Ar), 130.07 (o-Ar), 134.81 (p-Ar), 154.12 (i-benzyl), 154.90 (i-Ar), 157.30 (o-py), 166.46 (N=C).

Example 20

Evaluation of the Catalytic Activity of ($^{Mes}$PDI)Co-Benzyl

This experiment was performed in a scintillation vial using 0.100 g (0.891 mmol) of 1-octene, 0.100 g (0.449 mmol, 0.5 equiv) of MD$^H$M and 0.002 g (0.004 mmol, 1 mol %) of ($^{Mes}$PDI)Co-benzyl. The reaction was monitored by GC and NMR spectroscopy and quenched via exposure to air prior to analysis. 43% conversion to products was observed after 15 minutes, and >98% after 1 hour.

Example 21A-21F

Crosslinking of Polysiloxanes with Olefins Using ($^{Mes}$PDI)CoCH$_3$

A 20 mL scintillation vial was charged with 0.002 g (0.004 mmol, 2000 ppm catalyst loading) of ($^{Mes}$PDI)CoCH$_3$ and the olefin (see Table 8 for specific amounts). The mixture was stirred until a homogenous pink solution was obtained. This step typically required between 5 and 20 minutes of stirring. The polysiloxane (1:0.75 ratio of C=C to Si—H, Table 8) was then added to the reaction vessel and the mixture was stirred in an oil bath at 65° C. for 4-6 hours. The resulting gel was crushed into a powder using a mortar and pestle, washed with hexanes to remove the alkane by-product, and dried in vacuo overnight.

General Procedure for the Quantification of Unreacted Si—H Groups in the Crosslinked Polysiloxanes.

A 100 mL round-bottom flask was charged with the polymer sample (Table 7) and excess (0.040-0.060 g) KOH. A vacuum adapter was attached to the flask and the latter was evacuated. Approximately 20 mL of degassed ethanol was distilled over to the reaction flask, and the reaction was stirred at room temperature for 3 hours. The gas evolved from the reaction was quantified using a Toepler pump (volume=19.8 mL; temperature=297 K). To correct for any N$_2$ left in the reaction, the amount of H$_2$ was measured as the combustible component of the gas collected (Table 7). Each sample was analyzed twice.

TABLE 7

Determination of Unreacted SiH in the Crosslinked Polysiloxanes

| EXAMPLE | SAMPLE #1, g | SAMPLE #1, mmole SiH | SAMPLE #2, g | SAMPLE #2, mmole SiH | Average mmole SiH/g | SiH Conversion, % |
|---|---|---|---|---|---|---|
| 21A | 0.136 | 0.129 | 0.152 | 0.167 | 1.024 | 73.7 |
| 21B | 0.321 | 0.080 | 0.43 | 0.10 | 0.241 | 89.2 |
| 21C | 0.564 | 0.065 | 0.238 | 0.020 | 0.100 | 95.2 |
| 21D | 0.709 | 0.069 | 0.411 | 0.036 | 0.092 | 93.7 |

Each of the hexane-extracted samples was analyzed by nuclear magnetic resonance (NMR) spectroscopy on a Bruker AVANCE 400WB Spectrometer operating at field strength of 9.40T; $^1$H's resonate at 400 MHz. Single pulse excitation (SPE) pulse sequence with magic angle spinning (MAS) was used with a delay of 150 seconds for the {$^1$H—$^{13}$C} SPE/MAS NMR spectra or a delay of 300 seconds for the {$^1$H-$^{29}$Si} SPE/MAS NMR spectra. Cross-polarization (CP) pulse sequence with magic angle spinning (MAS) was used with a delay of 10 seconds and a contact time of 5 ms for the {$^1$H—$^{13}$C} CP/MAS NMR spectra. About 0.1 g of each sample was packed into a 4 mm zirconia ($ZrO_2$) rotor with a Kel-F cap and the rotor spun at ~8 to 10.8 kHz for the $^{29}$Si data and ~10.8 kHz for the $^{13}$C data. The number of co-added scans were 1000 ($^{13}$C) or 512 ($^{29}$Si) for the SPE data and 16,000 for the CP/MAS $^{13}$C data. The processing parameters used were zero-filling to 4× and LB of 5 or 15 Hz for the $^{13}$C data or 30 Hz for the $^{29}$Si data.

TABLE 8

Crosslinking of polysiloxanes with olefins using $(^{Mes}PDI)CoCH_3$.

| EXAMPLE | Polysiloxane | Olefin | Polymer Yield |
|---|---|---|---|
| 21A | $MD_{15}D^H{}_{30}M$ (0.500 g) | 1-Octene (0.750 g) | 0.860 g (98%) |
| 21B | $MD_{15}D^H{}_{30}M$ (0.285 g) | 1-Octadecene (0.965 g) | 0.733 g (96%) |
| 21C | $MD_{15}D^H{}_5M$ (0.825 g) | 1-Octene (0.425 g) | 0.985 g (95%) |
| 21D | $MD_{15}D^H{}_5M$ (0.580 g) | 1-Octadecene (0.672 g) | 0.868 g (95%) |
| 21E | $MD_{15}D^H{}_5M$ (0.665 g) and $M^HD_{45}M^H$ (0.225 g) | 1-Octene (0.360 g) | 0.894 g (84%) |
| 21F | $MD_{15}D^H{}_5M$ (0.490 g) and $M^HD_{45}M^H$ (0.165 g) | 1-Octadecene (0.595 g) | 0.789 g (83%) |

$^{13}$C NMR Results
1. Olefin: 1-Octene

The chemical shifts and their assignments of the $^{13}$C SPE/MAS and CP/MAS NMR spectra of samples from Examples 21A, 21C, and 21E are summarized in Table 9. The spectra show a multiple of signals observed in three distinct chemical shift regions, δ 2 to δ-2 consistent with methyl on silicon ($CH_3Si$), δ 14 to δ 35 consistent with linear type hydrocarbons and δ 124 to δ 135 due to olefinic ($sp^2$) carbons. No peak was observed at ~δ 115 indicating no residual unreacted 1-octene. A comparison of the data from the two different experiments shows significant differences. There is a significant loss in area for the $CH_2$, $CH_3$, and olefinic carbons. The results are consistent with the more mobile phase in the sample being saturated and unsaturated hydrocarbons, while the more rigid phase would consist of the following type structure, $\equiv SiCH_2CH_2CH_2(CH_2)_2CH_2CH_2CH_2Si$. However, in the CP experiment there is still a large amount of olefinic signals. This result suggests the presence of unsaturated structures with internal double bonds (note that the double bond can be in positions 2 thru 6), $\equiv SiCH_2CH_2CH=CH(CH_2)_2CH_2CH_2CH_3$.

The two signals observed at δ 125 and δ 131 due to the olefinic carbons are found with approximate equal intensity. The signals are consistent with the double bond being in position 2 or 6. The CP data for sample 21A show a very weak peak observed at δ 14 indicating that if the double bond is in position 6 the major configuration must be trans. The methyl group in the trans 6-position, —CH=CHCH$_3$, would overlap the signal observed at δ 18. The weaker signals observed around δ 130 are consistent with the double bond being in position 3, 4, or 5.

TABLE 9

$^{13}$C SPE/MAS & CP/MAS NMR Intensity Data for 1-Octene Samples (Examples 21A, 21C, 21E)

| Chemical Shift (δ, ppm) | Assignment | Example 21A SPE | Example 21A CP | Example 21C SPE | Example 21C CP | Example 21E SPE | Example 21E CP |
|---|---|---|---|---|---|---|---|
| 133 to 125 | sp$^2$ carbons: double bond | 6.35 | 3.19 | 4.70 | 2.06 | 3.89 | 1.88 |
| 109.3 | | | | 1.07 | | 1.83 | |
| 40 to 20* | —CH$_2$— groups | 15.06 | 6.99 | 10.22 | 5.94 | 10.52 | 5.96 |
| 36.9 | | 2.44 | trace | | 0.29 | | |
| 33.6 | Si—CH$_2$CH$_2$CH$_2$— & —CH$_2$CH$_2$CH$_3$ (#3 & #6) | 2.87 | 2.47 | | 1.91 | | |

TABLE 9-continued $^{13}$C SPE/MAS & CP/MAS NMR Intensity Data for
1-Octene Samples (Examples 21A, 21C, 21E)

| Chemical Shift (δ, ppm) | Assignment | Example 21A SPE | Example 21A CP | Example 21C SPE | Example 21C CP | Example 21E SPE | Example 21E CP |
|---|---|---|---|---|---|---|---|
| 30.3 | 4$^{th}$ —CH$_2$— from either end | 3.33 | 1.09 | 1.16 | | | |
| 27.8 | | 0.96 | 0.31 | 0.27 | | — | trace |
| 23.7 | Si—CH$_2$CH$_2$— & —CH$_2$$\underline{CH_3}$ (#2 & #7) | 5.17 | 2.73 | 2.31 | | | |
| 18.1 | SiCH$_2$— (#1) | 2.00 | 2.00 | 2.00 | 2.00 | 2.00 | 2.00 |
| 14.8 | $\underline{CH_3}$— (#8) | 2.98 | 0.22 | 1.38 | — | 1.41 | — |
| 2 to −3 | Si$\underline{CH_3}$ | 9.98 | 5.28 | 20.62 | 6.33 | 2963 | 6.39 |

*The areas of all the methylene carbons are grouped together.

2. Olefin: 1-Octadecene

The chemical shifts and their assignments of the $^{13}$C SPE/MAS and CP/MAS NMR spectra of samples from Examples 21B, 21D and 21F are summarized in Table 10. The spectra are very similar those of the 1-octene crosslinked samples in that they show a multiple of signals in three distinct chemical shift regions, δ 2 to δ −2 consistent with methyl on silicon (CH$_3$Si), δ 14 to δ 35 consistent with linear type hydrocarbons and δ 124 to δ 135 due to olefinic (sp$^2$) carbons. However, the signal observed at ~δ 30 is significantly stronger due to the higher number of methylene groups (CH$_2$) in the 1-octadecene starting material. A second difference is observed in the olefinic chemical shift range. The peak observed at ~δ 125 is not observed with the same intensity as the peak at ~δ 131. This result would suggest the double bond is not near one of the ends but is internal.

The following list summarizes the similarities to the results of the 1-octene data.
  No peak is observed at ~δ 115 indicating no residual unreacted 1-octadecene.

The SPE and CP data show significant loss in peak area for the CH$_2$, CH$_3$, and olefinic carbons.

The more mobile phase in the sample being saturated and unsaturated hydrocarbons, while the more rigid phase would consist of the following type structure, ≡SiCH$_2$CH$_2$CH$_2$(CH$_2$)$_{12}$CH$_2$CH$_2$CH$_2$Si≡.

The CP experiment shows a large amount of olefinic signals indicating the following type structure may be present (note that the double bond could be in positions 2 thru 16), ≡SiCH$_2$CH$_2$CH=CH(CH$_2$)$_{12}$CH$_2$CH$_2$CH$_3$. The loss in area of the CH$_3$ peak observed at δ 15 in the CP/MAS experiment could be due to the combination of the methyl group being associated to a hydrocarbon type molecule in the mobile phase and from the following type structure; ≡SiCH$_2$CH=CHCH$_2$(CH$_2$)$_{13}$CH$_3$, and the lost intensity is due to the group being at the end of the molecule resulting in greater mobility. The methyl group is farther from the point of cross-linking.

TABLE 10

$^{13}$C SPE/MAS & CP/MAS NMR Intensity Data of 1-Octadecene Samples (Examples 21B, 21D and 21F)

| Chemical Shift (δ, ppm) | Tentative Assignment | Example 21B SPE | Example 21B CP | Example 21D SPE | Example 21D CP | Example 21F SPE | Example 21F CP |
|---|---|---|---|---|---|---|---|
| 133 to 125 | sp carbons: double bond | 3.47 | 1.73 | 3.69 | 2.01 | 6.74 | 2.41 |
| 109.3 | | | | 1.96 | | 1.66 | |
| 40 to 20* | —CH$_2$— groups | 37.67 | 13.25 | 30.89 | 17.46 | 38.08 | 20.14 |
| 36.9 | | — | — | — | — | | |
| 33.6 | Si—CH$_2$CH$_2$CH$_2$— & —CH$_2$CH$_2$$\underline{CH_3}$ (#3 & #6) | | 2.58 | | | | |
| 30.3 | 4$^{th}$ —CH$_2$— from either end | | 8.33 | | | | |
| 27.8 | | trace | trace | trace | trace | | |
| 23.7 | Si—CH$_2$CH$_2$— & —CH$_2$$\underline{CH_3}$ (#2 & #7) | 5.28 | 2.34 | | | | |
| 18.1 | SiCH$_2$— (#1) | 2.00 | 2.00 | 2.00 | 2.00 | 2.00 | 2.00 |
| 14.8 | $\underline{CH_3}$— (#8) | 2.60 | — | 1.70 | — | 2.87 | |
| 2 to −3 | Si$\underline{CH_3}$ | 6.90 | 3.58 | 19.91 | 4.52 | 26.01 | 5.24 |

*The areas of all the methylene carbons are grouped together.

$^{29}$Si NMR Results

Chemical shifts and assignments of the $^{29}$Si SPE/MAS NMR spectra for the six samples of Example 21 are summarized in Table 11. The signal observed at δ-26 is assigned to a D* with the organofunctional group having the double bond in the allylic or 2 position, ≡SiCH$_2$CH=CHCH$_2$(CH$_2$)$_x$CH$_3$. This signal is very strong in Example 21A compared to the spectra of the other samples. Also, there appears to be a slight trend in this peak being slighty larger when the samples are prepared with 1-octene than with 1-octadecene. The integral of this signal is grouped with the stronger signals observed at δ -22 because of the peak overlap for the majority of the samples.

The spectra of the two samples (Examples 21A and 21B) prepared with the SiH fluid, MD$_{30}$D$^H_{15}$M show a large amount of what could be a combination of cyclic D$_3$ and D$^1$ type species and do not contain a signal at δ-35.

TABLE 11

$^{29}$Si SPE/MAS NMR Intensity Data for Example 21A-21F

| Chemical Shift (δ, ppm) | Assignment | Ex 21A | Ex 21B | Ex 21C | Ex 21D | Ex 21E | Ex 21F |
|---|---|---|---|---|---|---|---|
| 7 | M | 2.00 | 2.00 | 2.00 | 2.00 | 2.00 | 2.00 |
| -5 to -15 | Cyclic D$_3$ & D$^1$ | 8.05 | 10.28 | 0.97 | 0.96 | 0.87 | 0.73 |
| -22 | D & D* | 39.18 | 42.28 | 22.36 | 23.45 | 25.41 | 28.58 |
| -26 | D* | | | | | | |
| -35 | D' | — | — | 0.59 | 0.33 | 0.43 | |
| -37 | D' | 8.15 | 2.76 | | | | 0.82 |
| -55 | T$^2$ | 0.85 | — | — | — | 0.10 | |
| -66 | T$^3$ | 0.76 | — | 0.22 | 0.22 | 0.18 | |

In terms of the rheological characteristics of the products, one would predict different moduli resulting from molecules dependent on the cross-linked densities and the chain lengths of the linking molecule.

Example 22

Synthesis of 2-octenyl-capped SL-6020 (SL6020-octenyl)

This Example illustrates the synthesis of a fluid alkenylated polysiloxane by using a stoichiometric excess of olefin relative to SiH. The reaction is depicted in the equation below.

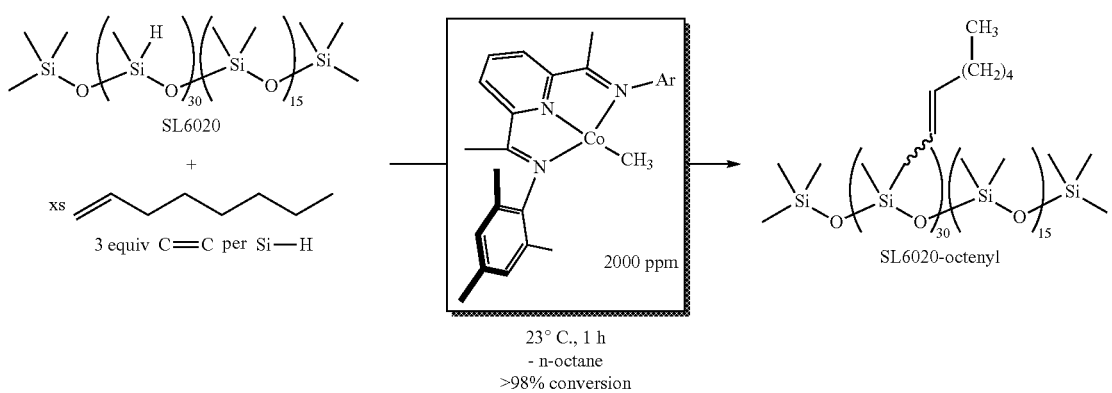

A 20 mL scintillation vial was charged with 1.000 g (8.91 mmol, 3 equiv per Si—H group) of 1-octene and 0.002 g (0.004 mmol, 2000 ppm) of ($^{Mes}$PDI)CoMe. The mixture was stirred until a homogeneous solution was obtained. 0.300 g of SL6020 (2.92 mmol SiH) was then added, and the reaction was stirred for 1 hour at room temperature and quenched by exposure to air. The volatiles were removed in vacuo, and the thick oily residue was analyzed by $^1$H, $^{13}$C and $^{29}$Si NMR spectroscopy. No unreacted Si—H was detected by NMR and IR spectroscopies as well as the degradation experiment with ethanolic KOH. A summary of the NMR data is presented below.

A 2:1 E/Z ratio was observed for the octenyl chains. $^1$H NMR (500 MHz, CDCl$_3$): δ=0.06 and 0.08 (s, 6H, SiCH$_3$), 0.87 (t, 3H, C$^8$H$_3$), 1.21-1.37 (m, 6H, C$^5$H$_2$C$^6$H$_2$C$^7$H$_2$), 1.44 (E, 7.4 Hz) and 1.49 (Z, 8.5 Hz) (d, 2H, C$^1$H$_2$), 1.97 (m, 2H, C$^4$H$_2$), 5.29 (m, 1H, SiCH=CH), 5.39 (m, 1H, SiCH=CH). {$^1$H} $^{13}$C NMR (125 MHz, CDCl$_3$): δ=−0.88 and 1.27 (SiCH$_3$); 14.23 (C$^8$); 19.27, 22.72, 22.80, 23.56, 27.21, 29.54, 29.70, 31.63, 31.81, 33.04 (E/Z CH$_2$); 123.88 (C$^2$—Z); 124.50 (C$^2$-E); 128.88 (C$^3$—Z); 130.34 (C$^3$-E). $^{29}$Si {$^1$H} NMR (125 MHz, CDCl$_3$): δ=−26.17, −21.74.

Example 23

Crosslinking of SL6020 and SL6020-Octenyl

This Example illustrates the crosslinking of octenyl capped SL6020 by addition of SL6020.

The reaction was performed in a manner similar to the crosslinking of polysiloxanes with α-olefins using 1.005 g of SL6020octenyl, 0.245 g of SL6020 (2:1 C=C:Si—H) and 0.002 g (0.004 mmol, 2000 ppm) of ($^{Mes}$PDI)CoCH$_3$. SiH conversion of 24±4% was determined when the crosslinked reaction product was subjected to the ethanolic KOH reaction and the evolved hydrogen was measured. In general, alkenyl capped polysiloxane like SL6020-octenyl can be reacted with a completely different polyhydridosiloxane to obtain a crosslinked product.

Examples 24A-24D

Olefin Isomerization Experiments

Example 24A shows that ($^{Mes}$PDI)CoCH$_3$ does not isomerize 1-octene. A scintillation vial was charged with 0.100 g (0.891 mmol) of 1-octene and 0.004 g (0.008 mmol, 1 mol %) of ($^{Mes}$PDI)CoCH$_3$. The solution was stirred for one hour at room temperature and then quenched by exposure to air. The $^1$H NMR spectrum of the product showed only 1-octene and traces of free ligand and no evidence for olefin isomerization.

Example 24B shows that 1-octene isomerization was not observed with ($^{Mes}$PDI)CoCH$_3$ and trace amounts of hydridotrisiloxane, MD$^H$M.

This experiment was performed in the same manner as the experiment described above (Example 24A) using 0.100 g (0.891 mmol) of 1-octene, 0.004 g (0.008 mmol, 1 mol %) of ($^{Mes}$PDI)CoCH$_3$, and 0.014 g (0.063 mmol, 7 mol %) of MD$^H$M. The $^1$H NMR spectrum of the product showed only 1-octene, traces of free ligand and 1-bis(trimethylsiloxy)methylsilyl-2-octene, and no evidence for olefin isomerization.

Example 24C illustrates isomerization of N,N-dimethylallylamine, (CH$_3$)$_2$NCH$_2$CH=CH$_2$, using ($^{Mes}$PDI)CoCH$_3$.

A J. Young tube was charged with 0.017 g (0.20 mmol) of N,N-dimethylallylamine, 0.002 g (0.004 mmol, 2 mol %) of ($^{Mes}$PDI)CoCH$_3$ and approximately 0.7 mL of benzene-d$_6$. The solution was allowed sit at room temperature and monitored using $^1$H NMR spectroscopy. Isomerization of the starting material to N,N-dimethyl-1-propenylamine, (CH$_3$)$_2$NCH=CHCH$_3$, was 20% complete after 8 hours and 65% after 46 hours.

Example 24D illustrates isomerization of N,N-dimethylallylamine, (CH$_3$)$_2$NCH$_2$CH=CH$_2$, using ($^{Mes}$PDI)CoCH$_3$ and trace amounts of the hydrido trisiloxane, MD$^H$M.

This reaction was carried out in a manner similar to the experiment described above (Example 24C) using 0.091 g (1.1 mmol) of N,N-dimethylallylamine, 0.003 g (0.006 mmol, 0.6 mol %) of ($^{Mes}$PDI)CoCH$_3$ and 0.006 g (0.03 mmol, 3 mol %) of MD$^H$M. Isomerization of the starting material to N,N-dimethyl-1-propenylamine, (CH$_3$)$_2$NCH=CHCH$_3$ was 90% complete after 8 hours and >95% after 24 hours.

Example 25A-25C

Silylation of Propylene with Different Silanes Using ($^{Mes}$PDI)CoCH$_3$

This reaction was carried out in a manner similar to the silylation of 1-butene using 0.11 mmol of silane (0.025 g of MD$^H$M, 0.018 g of (EtO)$_3$SiH or 0.015 g of (OEt)$_2$CH$_3$SiH) 0.001 g (0.002 mmol) of ($^{Mes}$PDI)CoCH$_3$ and 5.6 mmol (50 equiv) of propylene. The non-volatiles were analyzed by NMR spectroscopy.

TABLE 12

Product Distribution for the Silylation of Propylene.

| Silane | [Si]-allyl | [Si]-propyl | Disproportionation Product |
|---|---|---|---|
| Ex 25A: MD$^H$M | 82% | 18% | None |
| Ex 25B: TES | 40% | 20% | 40% |
| Ex 25C: Me(OEt)$_2$SiH | 60% | 30% | 10% |

Characterization of Products of Example 25A 3-bis(trimethylsiloxy)methylsilyl-1-propene $^1$H NMR (CDCl$_3$): δ=0.03 (s, 3H, (OTMS)$_2$SiCH$_3$), 0.09 (s, 18H, OSi(CH$_3$)$_3$), 1.49 (d, J=8.1 Hz, 2H, SiCH$_2$CH=CH), 4.86 (d, J=6.3 Hz, 1H, CH$_2$CH=C(H)H), 4.88 (d, J=15 Hz, 1H, CH$_2$CH=C(H)H), 5.77 (m, 1H, CH$_2$CH=CH$_2$). $^{13}$C {$^1$H} NMR (CDCl$_3$): δ=−0.77 ((OTMS)$_2$ SiCH$_3$), 1.97 (OSi(CH$_3$)$_3$), 25.82 (SiCH$_2$CH=CH), 113.72 (CH$_2$CH=CH$_2$), 134.28 (CH$_2$CH=CH$_2$).

1-bis(trimethylsiloxy)methylsilylpropane $^1$H NMR (CDCl$_3$): δ=0.00 (s, 3H, (OTMS)$_2$SiCH$_3$), 0.09 (s, 18H, OSi(CH$_3$)$_3$), 0.46 (m, 2H, SiCH$_2$CH$_2$CH$_3$), 0.95 (t, 3H, SiCH$_2$CH$_2$CH$_3$), 1.36 (m, 2H, SiCH$_2$CH$_2$CH$_3$). $^{13}$C {$^1$H} NMR (CDCl$_3$): δ=−0.07 ((OTMS)$_2$SiCH$_3$), 1.97 (OSi (CH$_3$)$_3$), 16.75 (SiCH$_2$CH$_2$CH$_3$), 18.05 (SiCH$_2$CH$_2$CH$_3$), 20.37 (SiCH$_2$CH$_2$CH$_3$).

Characterization of Products of Example 25B 3-triethoxysilyl-1-propene $^1$H NMR (CDCl$_3$): δ=1.22 (t, 9H, OCH$_2$CH$_3$), 1.67 (d, 2H, SiCH$_2$CH=CH), 3.84 (q, 6H, OCH$_2$CH$_3$), 4.90-5.05 (d, 2H, CH$_2$CH=CH$_2$), 5.81 (m, 1H, CH$_2$CH=CH$_2$). $^{13}$C {$^1$H} NMR (CDCl$_3$): δ=18.36 (OCH$_2$CH$_3$), 19.34 (SiCH$_2$CH=CH), 58.73 (OCH$_2$CH$_3$), 114.85 (CH$_2$CH=CH$_2$), 132.80 (CH$_2$CH=CH$_2$).

1-triethoxysilylpropane $^1$H NMR (CDCl$_3$): δ=0.63 (m, 2H, SiCH$_2$CH$_2$CH$_3$), 0.97 (t, 3H, SiCH$_2$CH$_2$CH$_3$), 1.22 (t, 9H, OCH$_2$CH$_3$), 1.45 (m, 2H, SiCH$_2$CH$_2$CH$_3$). $^{13}$C {$^1$H} NMR (CDCl$_3$): δ=10.94 (SiCH$_2$CH$_2$CH$_3$), 12.92 (SiCH$_2$CH$_2$CH$_3$), 16.50 (SiCH$_2$CH$_2$CH$_3$), 18.43 (OCH$_2$CH$_3$), 58.40 (OCH$_2$CH$_3$).

Characterization of Products of Example 25C 3-diethoxymethylsilyl-1-propene $^1$H NMR (CDCl$_3$): δ=0.11 (s, 3H, SiCH$_3$), 1.19 (t, 6H, OCH$_2$CH$_3$), 1.63 (d, 2H, SiCH$_2$CH=CH), 3.76 (q, 4H, OCH$_2$CH$_3$), 4.88 (d, 1H, CH$_2$CH=C(H)H), 4.93 (d, 1H, CH$_2$CH=C(H)H), 5.80 (m, 1H, CH$_2$CH=CH$_2$). $^{13}$C {$^1$H} NMR (CDCl$_3$): δ=−5.19 (SiCH$_3$), 18.44 (OCH$_2$CH$_3$), 21.92 (SiCH$_2$CH=CH), 58.41 (OCH$_2$CH$_3$), 114.45 (CH$_2$CH=CH$_2$), 133.36 (CH$_2$CH=CH$_2$).

1-diethoxymethylsilylpropane $^1$H NMR (CDCl$_3$): δ=0.08 (s, 3H, SiCH$_3$), 0.59 (m, 2H, SiCH$_2$CH$_2$CH$_3$), 0.94 (t, 3H, SiCH$_2$CH$_2$CH$_3$), 1.19 (t, 6H, OCH$_2$CH$_3$), 1.38 (m, 2H, to SiCH$_2$CH$_2$CH$_3$), 3.76 (q, 4H, OCH$_2$CH$_3$). $^{13}$C {$^1$H} NMR (CDCl$_3$): δ=−4.76 (SiCH$_3$), 16.37 (SiCH$_2$CH$_2$CH$_3$), 16.53 (SiCH$_2$CH$_2$CH$_3$), 18.07 (SiCH$_2$CH$_2$CH$_3$), 18.50 (OCH$_2$CH$_3$), 58.13 (OCH$_2$CH$_3$).

Example 26

Reusability of the Initial Charge of ($^{Mes}$PDI)CoMe for Catalysis

A 20 mL scintillation vial was charged with 0.100 g (0.891 mmol) of 1-octene and 0.100 (0.449 mmol) of MD'M. 0.001 g (0.002 mmol) of ($^{Mes}$PDI)CoMe was then added, and the reaction was stirred at room temperature. An aliquot of the reaction was analyzed by GC after 30 min, which established complete conversion of the substrates to the allylsilane product. The reaction vial containing the allylsilane product was then charged with another 0.100 g of 1-octene and 0.100 g of MD'M. Complete conversion (based on GC analysis) of the second batch of substrates was observed after stirring the reaction for one hour at room temperature.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (I) or an adduct thereof;

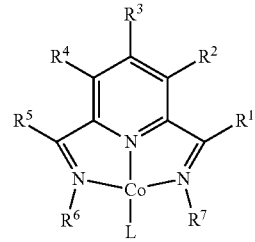

(I)

wherein each occurrence of R$^1$, R$^2$, R$^3$, R$^4$, and R$^5$ is independently hydrogen, C1-C18 alkyl, C1-C18 substituted alkyl, aryl, substituted aryl, or an inert substituent, wherein R$^1$-R$^5$, other than hydrogen, optionally contain at least one heteroatom;

each occurrence of R$^6$ and R$^7$ is independently C1-C18 alkyl, C1-C18 substituted alkyl, aryl or substituted aryl, wherein R$^6$ and R$^7$ optionally contain at least one heteroatom;

optionally any two of R$^1$, R$^2$, R$^3$, R$^4$, R$^5$, R$^6$ and R$^7$ vicinal to one another taken together may form a ring being a substituted or unsubstituted, saturated, or unsaturated cyclic structure; and L is hydroxyl, chloride, bromide, or a C1-C18 alkyl, C1-C18 substituted alkyl, aryl, or substituted aryl group, an alkaryl group, an aralkyl group, —H, SiR$_3$ where R is an alkyl, aryl, or siloxanyl group, or component (a) wherein L optionally contains at least one heteroatom.

2. A process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex selected from the group consisting of Formula (IV), Formula (V), Formula (VI), Formula (VII), or an adduct thereof

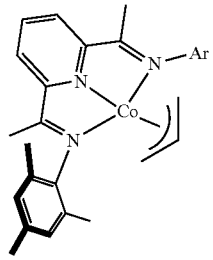

(Formula IV)

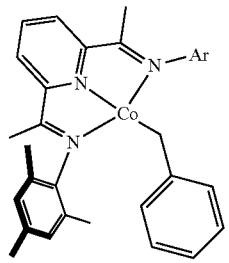

(Formula V)

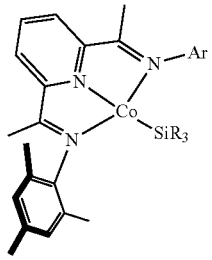
(Formula VI)

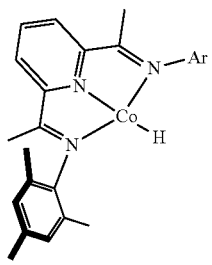
(Formula VII)

wherein R is an alkyl, aryl, or siloxanyl group.

3. The process of claim 1 further comprising removing the complex and/or derivatives thereof from the dehydrogenative silylated product.

4. The process of claim 1 wherein the dehydrogenatively silylated product comprises a silane or siloxane containing a silyl group and an unsaturated group.

5. The process of claim 4, wherein the unsaturated group is in the alpha or beta position relative to the silyl group.

6. The process of claim 1 wherein the molar ratio of the unsaturated group in said component (a) relative to the silyl-hydride functional group in said component (b) is less than equal to 1:1.

7. The process of claim 6 wherein the silane or siloxane of the dehydrogenatively silylated product contains one silyl group derived from component (b).

8. The process of claim 6 wherein the dehydrogenatively silylated product contains two or more terminal silyl groups derived from component (b).

9. The process of claim 6, wherein said process produces an α,ω-substituted alkane or alkene diol from a parent α,ω-bis(silyl) substituted alkane or alkene.

10. The process of claim 1 wherein the molar ratio of the unsaturated group in said component (a) relative to the silyl-hydride functional group in said component (b) is greater than 1:1.

11. The process of claim 10 wherein the silane or siloxane contains two or more silyl groups derived from component (b).

12. The process of claim 1 wherein said component (a) is a mono-unsaturated compound.

13. The process of claim 1 wherein said component (a) is selected from the group consisting of an olefin, a cycloalkene, an alkyl-capped allyl polyether, a vinyl-functional alkyl-capped allyl or methallyl polyether, an alkyl-capped terminally unsaturated amine, an alkyne, terminally unsaturated acrylate or methacrylate, unsaturated aryl ether, vinyl-functionalized polymer or oligomer, vinyl-functionalized silane, vinyl-functionalized silicone, unsaturated fatty acids, unsaturated esters, and combinations thereof.

14. The process of claim 13 wherein said component (a) is selected from the group consisting of N,N-dimethylallyl amine, allyloxy-substituted polyethers, cyclohexene, linear alpha olefins, internal olefins, branched olefins, unsaturated polyolefins, a vinyl siloxane of the Formula (XII), and combinations thereof, wherein Formula (XII) is

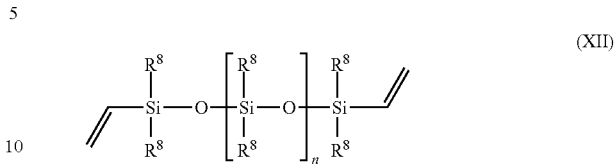
(XII)

wherein each occurrence of $R^8$ is independently a C1-C18 alkyl, C1-C18 substituted alkyl, vinyl, aryl, or a substituted aryl, and n is greater than or equal to zero.

15. The process of claim 1 wherein said component (b) is selected from the group consisting of $R_aSiH_{4-a}$, $(RO)_aSiH_{4-a}$, $HSiR_a(OR)_{3-a}$, $R_3Si(CH_2)_f(SiR_{2O})_kSiR_2H$, $(RO)_3Si(CH_2)_f(SiR_{2O})_kSiR_2H$, $Q_uT_vT_p^{H}D_wD^H_xM^H_yM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $HR'_2SiO_{1/2}$, M is $R'_3SiO_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silyl hydride are satisfied.

16. The process of claim 15, wherein p, u, v, y, and z are from 0 to 10, w and x are from 0 to 100, wherein p+x+y equals 1 to 100.

17. The process of claim 1 wherein said component (b) has one of the following structures:

$R^1_a(R^2O)_bSiH$ (Formula XIII)

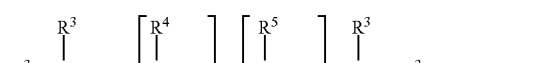
(Formula XIV)

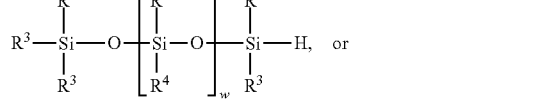
(Formula XV)

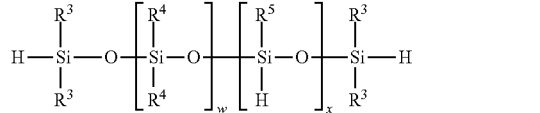
(Formula XVI)

wherein each occurrence of $R^1$, $R^2$, $R^3$, $R^4$, and $R^5$ is independently a C1-C18 alkyl, C1-C18 substituted alkyl, aryl, or substituted aryl, $R^6$ is hydrogen, a C1-C18 alkyl, C1-C18 substituted alkyl, aryl, or substituted aryl, x and w are independently greater than or equal to 0 (x is at least equal to 1 for Formula X), and a and b are integers from 0 to 3 provided that a+b=3.

18. The process of claim 1 wherein at least one of $R^6$ and $R^7$ is

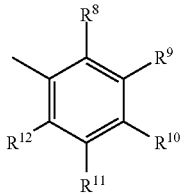

wherein each occurrence of $R^8$, $R^9$, $R^{10}$, $R^{11}$, and $R^{12}$ is independently hydrogen, C1-C18 alkyl, C1-C18 substituted alkyl, aryl, substituted aryl, or an inert substituent, wherein $R^8$-$R^{12}$, other than hydrogen, optionally contain at least one heteroatom.

19. The process of claim 18 wherein $R^8$ and $R^{12}$ are independently methyl, ethyl or isopropyl groups and $R^{10}$ is hydrogen or methyl.

20. The process of claim 19 wherein $R^8$, $R^{10}$, and $R^{12}$ are each methyl.

21. The process of claim 1 wherein $R^1$ and $R^5$ are independently methyl or phenyl groups.

22. The process of claim 1 wherein $R^2$, $R^3$ and $R^4$ are hydrogen.

23. The process of claim 1 wherein the complex is immobilized on a support.

24. The process of claim 23 wherein the support is selected from the group consisting of carbon, silica, alumina, $MgCl_2$, zirconia, polyethylene, polypropylene, polystyrene, poly (aminostyrene), sulfonated polystyrene, dendrimers, and combinations thereof.

25. The process of claim 23 wherein at least one of $R^1$ to $R^7$ contains a functional group that covalently bonds with the support.

26. The process of claim 1 wherein the catalyst is generated in-situ by contacting a catalyst precursor with an activator in the presence of a liquid medium containing at least one component selected from the group consisting of a solvent, the silyl hydride, the compound containing at least one unsaturated group, and combinations thereof, wherein the catalyst precursor is represented by structural Formula (VIII)

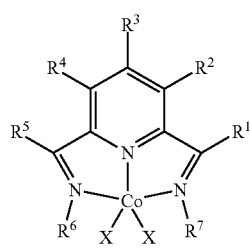

(VIII)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;

each occurrence of $R^6$ and $R^7$ is independently C1-C18 alkyl, C1-C18 substituted alkyl, aryl or substituted aryl, wherein $R^6$ and $R^7$ optionally contain at least one heteroatom;

optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and X is an anion selected from the group consisting of $F^-$, $Cl^-$, $Br^-$, $I^-$, $CF_3R^{40}SO_3^-$ or $R^{50}COO^-$, wherein $R^{40}$ is a covalent bond or a C1-C6 alkylene group, and $R^{50}$ is a C1-C10 hydrocarbyl group;

and wherein the activator is a reducing agent or an alkylating agent selected from the group consisting of $NaHBEt_3$, $CH_3Li$, DIBAL-H, LiHMDS, MeMgBr, EtMgCl, and combinations thereof.

27. The process of claim 1 wherein the reaction is conducted under an inert atmosphere.

28. The process of claim 1 wherein the reaction is conducted in the presence of a solvent selected from the group consisting of hydrocarbons, halogenated hydrocarbons, ethers, and combinations thereof.

29. The process of claim 1 wherein the reaction is carried out at a temperature of –40° C. to 200° C.

30. A composition produced by the process of claim 1, wherein the composition contains the catalyst or derivatives thereof.

31. The composition of claim 30 comprising at least one component selected from the group consisting of silanes, silicone fluids and crosslinked silicones.

32. A compound of Formula (II)

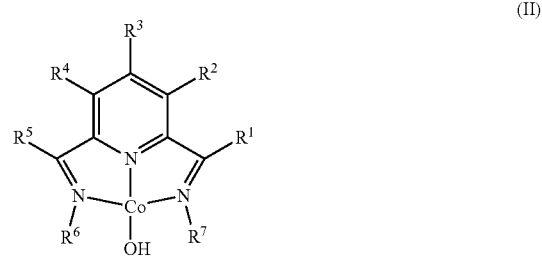

(II)

wherein each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;

each occurrence of $R^6$ and $R^7$ is independently C1-C18 alkyl, C1-C18 substituted alkyl, aryl or substituted aryl, wherein $R^6$ and $R^7$ optionally contain at least one heteroatom; and optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure.

33. A process for producing a dehydrogenatively silylated product comprising reacting a mixture comprising (a) an unsaturated compound containing at least one unsaturated functional group, (b) a silyl hydride containing at least one silylhydride functional group, and (c) a catalyst, optionally in the presence of a solvent, in order to produce the dehydrogenatively silylated product, wherein the catalyst is a complex of the Formula (III) or an adduct or salt thereof;

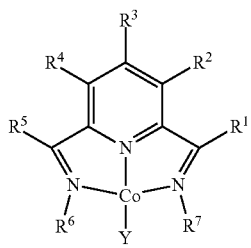

(III)

wherein
- each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;
- each occurrence of $R^6$ and $R^7$ is independently C1-C18 alkyl, C1-C18 substituted alkyl, aryl or substituted aryl, wherein $R^6$ and $R^7$ optionally contain at least one heteroatom;
- optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and
- Y is a neutral ligand optionally containing at least one heteroatom;
- and wherein Formula III is a neutral, cationic, or anionic complex.

34. The process of claim 33 further comprising removing the complex and/or derivatives thereof from the dehydrogenatively silylated product.

35. The process of claim 33 wherein the dehydrogenatively silylated product comprises a silane or siloxane containing a silyl group and an unsaturated group.

36. The process of claim 35, wherein the unsaturated group is in the alpha or beta position relative to the silyl group.

37. The process of claim 33 wherein the molar ratio of the unsaturated group in said component (a) relative to the silylhydride functional group in said component (b) is less than 1:1.

38. The process of claim 37 wherein the silane or siloxane of the dehydrogenatively silylated product contains one silyl group derived from component (b).

39. The process of claim 33 wherein the molar ratio of the unsaturated group in said component (a) relative to the silylhydride functional group in said component (b) is equal to or greater than 1:1.

40. The process of claim 39 wherein the silane or siloxane contains two or more silyl groups derived from component (b).

41. The process of claim 33 wherein said component (a) is a mono-unsaturated compound.

42. The process of claim 33 wherein said component (a) is selected from the group consisting of an olefin, a cycloalkene, an alkyl-capped allyl polyether, a vinyl-functional alkyl-capped allyl or methallyl polyether, an alkyl-capped terminally unsaturated amine, an alkyne, terminally unsaturated acrylate or methacrylate, unsaturated aryl ether, vinyl-functionalized polymer or oligomer, vinyl-functionalized silane, vinyl-functionalized silicone, unsaturated fatty acids, unsaturated esters, and combinations thereof.

43. The process of claim 33, wherein Y is selected from the group consisting of dinitrogen ($N_2$), phosphines, CO, nitrosyls, olefins, amines, ethers, and combinations thereof.

44. The process of claim 43, wherein Y is selected from the group consisting of $PH_3$, $PMe_3$, CO, NO, ethylene, THF, and $NH_3$.

45. The process of claim 42 wherein said component (a) is selected from the group consisting of N,N-dimethylallyl amine, allyloxy-substituted polyethers, cyclohexene, linear alpha olefins, internal olefins, branched olefins, unsaturated polyolefins, a vinyl siloxane of the Formula (XII), and combinations thereof, wherein Formula (XII) is

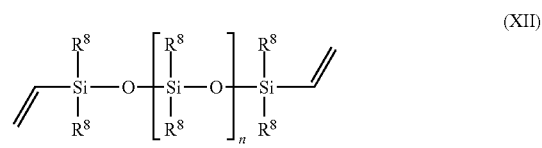

(XII)

wherein each occurrence of $R^8$ is independently a C1-C18 alkyl, C1-C18 substituted alkyl, vinyl, aryl, or a substituted aryl, and n is greater than or equal to zero.

46. The process of claim 33 wherein said component (b) is selected from the group consisting of $R_aSiH_{4-a}$, $(RO)_aSiH_{4-a}$, $HSiR_a(OR)_{3-a}$, $R_3Si(CH_2)_f(SiR_{2O})_kSiR_2H$, $(RO)_3Si(CH_2)_f(SiR_{2O})_kSiR_2H$, $Q_aT_vT_p^{H}D_wD^H_xM^H_yM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $HR'_2SiO_{1/2}$, M is $R'_3SiO_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silyl hydride are satisfied.

47. The process of claim 46, wherein p, u, v, y, and z are from 0 to 10, w and x are from 0 to 100, wherein p+x+y equals 1 to 100.

48. The process of claim 33 wherein said component (b) has one of the following structures:

$R^1_a(R^2O)_bSiH$      (Formula XIII)

$$R^3-\underset{\underset{R^3}{|}}{\overset{\overset{R^3}{|}}{Si}}-O-\left[\underset{\underset{R^4}{|}}{\overset{\overset{R^4}{|}}{Si}}-O\right]_w\left[\underset{\underset{H}{|}}{\overset{\overset{R^5}{|}}{Si}}-O\right]_x\underset{\underset{R^3}{|}}{\overset{\overset{R^3}{|}}{Si}}-R^3,$$ (Formula XIV)

$$R^3-\underset{\underset{R^3}{|}}{\overset{\overset{R^6}{|}}{Si}}-O-\left[\underset{\underset{R^4}{|}}{\overset{\overset{R^4}{|}}{Si}}-O\right]_w\underset{\underset{R^3}{|}}{\overset{\overset{R^3}{|}}{Si}}-H, \text{ or}$$ (Formula XV)

$$H-\underset{\underset{R^3}{|}}{\overset{\overset{R^3}{|}}{Si}}-O-\left[\underset{\underset{R^4}{|}}{\overset{\overset{R^4}{|}}{Si}}-O\right]_w\left[\underset{\underset{H}{|}}{\overset{\overset{R^5}{|}}{Si}}-O\right]_x\underset{\underset{R^3}{|}}{\overset{\overset{R^3}{|}}{Si}}-H$$ (Formula XVI)

wherein each occurrence of $R^1$, $R^2$, $R^3$, $R^4$, and $R^5$ is independently a C1-C18 alkyl, C1-C18 substituted alkyl, aryl, or substituted aryl, $R^6$ is hydrogen, a C1-C18 alkyl, C1-C18 substituted alkyl, aryl, or substituted aryl, x and w are independently greater than or equal to 0 (x is at least equal to 1 for Formula X), and a and b are integers from 0 to 3 provided that a +b=3.

49. The process of claim 33 wherein at least one of $R^6$ and $R^7$ is

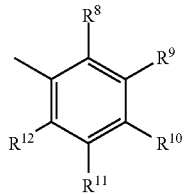

wherein each occurrence of $R^8$, $R^9$, $R^{10}$, $R^{11}$, and $R^{12}$ is independently hydrogen, C1-C18 alkyl, C1-C18 substituted alkyl, aryl, substituted aryl, or an inert substituent, wherein $R^8$-$R^{12}$, other than hydrogen, optionally contain at least one heteroatom.

50. The process of claim 49 wherein $R^8$ and $R^{12}$ are independently methyl, ethyl or isopropyl groups and $R^{10}$ is hydrogen or methyl.

51. The process of claim 50 wherein $R^8$, $R^{10}$, and $R^{12}$ are each methyl.

52. The process of claim 33 wherein $R^1$ and $R^5$ are independently methyl or phenyl groups.

53. The process of claim 33 wherein $R^2$, $R^3$ and $R^4$ are hydrogen.

54. The process of claim 33 wherein the complex is immobilized on a support.

55. The process of claim 54 wherein the support is selected from the group consisting of carbon, silica, alumina, $MgCl_2$, zirconia, polyethylene, polypropylene, polystyrene, poly (aminostyrene), sulfonated polystyrene, dendrimers, and combinations thereof.

56. The process of claim 55 wherein at least one of $R^1$ to $R^7$ contains a functional group that covalently bonds with the support.

57. The process of claim 33 wherein the catalyst is generated in-situ by contacting a catalyst precursor with an activator in the presence of a liquid medium containing at least one component selected from the group consisting of a solvent, the silyl hydride, the compound containing at least one unsaturated group, and combinations thereof, wherein the catalyst precursor is represented by structural Formula (VIII)

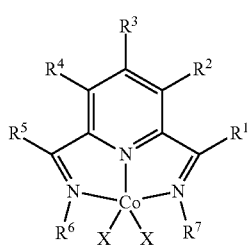

(VIII)

wherein
each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;

each occurrence of $R^6$ and $R^7$ is independently C1-C18 alkyl, C1-C18 substituted alkyl, aryl or substituted aryl, wherein $R^6$ and $R^7$ optionally contain at least one heteroatom;

optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and X is an anion selected from the group consisting of $F^-$, $Cl^-$, $Br^-$, $I^-$, $CF_3R^{40}SO_3^-$ or $R^{50}COO^-$, wherein $R^{40}$ is a covalent bond or a C1-C6 alkylene group, and $R^{50}$ is a C1-C10 hydrocarbyl group;

and wherein the activator is a reducing agent or an alkylating agent selected from the group consisting of NaHBEt$_3$, CH$_3$Li, DIBAL-H, LiHMDS, MeMgBr, EtMgCl, and combinations thereof.

58. The process of claim 33 wherein the reaction is conducted under an inert atmosphere.

59. The process of claim 33 wherein the reaction is conducted in the presence of a solvent selected from the group consisting of hydrocarbons, halogenated hydrocarbons, ethers, and combinations thereof.

60. The process of claim 33 wherein the reaction is carried out at a temperature of −40° C. to 200° C.

61. A process for producing a crosslinked material, comprising reacting a mixture comprising (a) a silyl-hydride containing polymer, (b) a mono-unsaturated olefin or an unsaturated polyolefin, or combinations thereof and (c) a catalyst, optionally in the presence of a solvent, in order to produce the crosslinked material, wherein the catalyst is a complex of the Formula (I) or an adduct thereof;

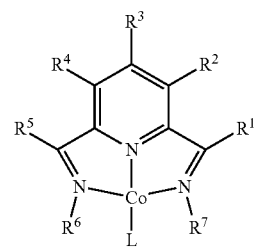

(I)

wherein
each occurrence of $R^1$, $R^2$, $R^3$, $R^4$, and $R^5$ is independently hydrogen, C1-C18 alkyl, C1-C18 substituted alkyl, aryl, substituted aryl, or an inert substituent, wherein $R^1$-$R^5$, other than hydrogen, optionally contain at least one heteroatom;

each occurrence of $R^6$ and $R^7$ is independently C1-C18 alkyl, C1-C18 substituted alkyl, aryl or substituted aryl, wherein $R^6$ and $R^7$ optionally contain at least one heteroatom;

optionally any two of $R^1$, $R^2$, $R^3$, $R^4$, $R^5$, $R^6$ and $R^7$ vicinal to one another taken together may form a ring being a substituted or unsubstituted, saturated, or unsaturated cyclic structure; and L is hydroxyl, chloride, bromide, or a C1-C18 alkyl, C1-C18 substituted alkyl, aryl, or substituted aryl group, an alkaryl group, an aralkyl group, —H, SiR$_3$ where R is an alkyl, aryl, or siloxanyl group, or component (a) wherein L optionally contains at least one heteroatom.

62. The process of claim 61 wherein the reaction is conducted under an inert atmosphere.

63. The process of claim 61 wherein the reaction is conducted in the presence of a solvent selected from the group consisting of hydrocarbons, halogenated hydrocarbons, ethers, and combinations thereof.

64. The process of claim 61 wherein the reaction is carried out at a temperature of −40° C. to 200° C.

65. The process of claim 1, further comprising adding additional unsaturated compound (a) and silyl hydride (b), and repeating said reacting step in the presence of the original charge of said catalyst (c) to produce additional dehydrogenatively silylated product.

* * * * *